(12) United States Patent
Discenzo

(10) Patent No.: US 10,042,334 B2
(45) Date of Patent: Aug. 7, 2018

(54) MICROBIAL MONITORING AND PREDICTION

(71) Applicant: Rockwell Automation Technologies, Inc., Mayfield Heights, OH (US)

(72) Inventor: Frederick M. Discenzo, Brecksville, OH (US)

(73) Assignee: ROCKWELL AUTOMATION TECHNOLOGIES, INC., Mayfield Heights, OH (US)

( * ) Notice: Subject to any disclaimer, the term of this patent is extended or adjusted under 35 U.S.C. 154(b) by 869 days.

(21) Appl. No.: 14/171,383

(22) Filed: Feb. 3, 2014

(65) Prior Publication Data

US 2014/0156050 A1 Jun. 5, 2014

Related U.S. Application Data

(63) Continuation of application No. 13/153,115, filed on Jun. 3, 2011, now Pat. No. 8,645,076.

(51) Int. Cl.
*G06F 19/00* (2018.01)
*G05B 13/04* (2006.01)
*C12M 1/34* (2006.01)
*C12M 1/36* (2006.01)

(52) U.S. Cl.
CPC .......... *G05B 13/04* (2013.01); *C12M 41/36* (2013.01); *C12M 41/48* (2013.01)

(58) Field of Classification Search
None
See application file for complete search history.

(56) References Cited

U.S. PATENT DOCUMENTS 7,153,470 B2   12/2006   Stockard et al.
7,581,434 B1 *  9/2009   Discenzo ........... G01N 33/2888
                                                         73/53.01

OTHER PUBLICATIONS

Office Action dated Jun. 11, 2012 for U.S. Appl. No. 13/153,115, 19 pages.
Wang et al., "Wireless Sensors in Agriculture and Food Industry—Recent Development and Future Perspective", Computer and Electronics in Agriculture, vol. 50, pp. 1-14, 2006.
Ivanov et al., "BioMEMS Sensor Systems for Bacterial Infection Detection—Progress and Potential" Biodrugs, vol. 20, issue 6, pp. 351-356, 2006.
Evans et al., "BioProcess Simulation: A New Tool for Process Development," Nature Biotechnology, vol. 6, pp. 200-203, 1988.
Office Action dated Oct. 25, 2012 for U.S. Appl. No. 13/153,115, 18 pages.
Lazcka et al. "Pathogen Detection: A perspective of traditional methods and biosensors" Biosensors and Bioelectronics (2007) vol. 22, pp. 1205-1217.
McMeekin et al., "Information Systems in Food Safety Management", International Journal of Food Microbiology (2006) vol. 112, pp. 181-194.
Office Action dated Apr. 12, 2013 for U.S. Appl. No. 13/153,115, 17 pages.

* cited by examiner

*Primary Examiner* — Lori A Clow
(74) *Attorney, Agent, or Firm* — Amin, Turocy & Watson, LLP

(57) ABSTRACT

Aspects describe capturing various bacteria levels within a process affected by microbial agents. A model of the process and a model of expected bacteria growth are analyzed and, based on the analysis, at least one process parameter is automatically modified to improve or optimize the product or process or other business or operational objectives. Also provided are at least two autonomous agents within the process. The at least two autonomous agents communicate and autonomously implement an action in an upstream stage and/or downstream stage within the process, wherein the at least two autonomous agents access the representation of the process and the biological representation and/or bio-chemical representation to implement the action.

20 Claims, 15 Drawing Sheets

MICROBIAL MONITORING AND PREDICTION

RELATED APPLICATION

This patent application is a continuation of U.S. patent application Ser. No. 13/153,115, filed Jun. 3, 2011, and entitled "MICROBIAL MONITORING AND PREDICTION," the entirety of which is incorporated herein by reference.

TECHNICAL FIELD

The subject disclosure relates generally to production processes and more particularly to automatically configuring and controlling a production process based at least in part upon modeling and predicting microbial levels within the production process.

BACKGROUND

Microbial elements exist in virtually every food manufacturing operation. The microbial elements (e.g., bacteria) are dynamic living organisms that are affected by their environment and in turn affect the environment in which they live. Bio-processes and other processes, such as food manufacturing, are affected both positively and negatively by the state of bacteria, molds, fungi, algae, and other bio-species and bio-chemical reactions. The techniques typically used to determine the level of bacteria can take days to perform (e.g., before the results from a laboratory test can be conducted and the results obtained). Often, processes are operated in an extremely conservative and inefficient manner to help insure low levels of bacteria. Occasionally, processes may be inadvertently operating with high bacteria levels due to inadequate or outdated information on bacteria present. For example, some processes may not have sensors to indicate the bacteria level. In other cases, the time from when a sample was extracted from the lab and the biological state determined may be excessive such that the laboratory test results do not reflect the current state of the production process. Further, products may need to be scrapped due to observed or suspected high bacteria levels.

A technique typically used to determine the level of bacteria in a process is to obtain a sample of the material from the process and place the sample in (or on) a nutrient under controlled conditions to permit any bio-agents present to grow and multiply (i.e., culture a sample from the production line). When organisms present in the culture dish have had sufficient time to grow and multiply, the organisms are visually and/or chemically inspected to determine the species and the quantity present. This process typically takes one or more days before the bacteria types and levels can be determined. The time necessary to determine micro-biological information is inadequate for feedback control of the process and is generally inadequate to permit changes in process set-points or for production scheduling. In addition, products often cannot be shipped until the bio-assay is completed with satisfactory results. Some other techniques (such as Polymerase Chain Reaction (PCR) and real-time PCR) can reduce the time to hours using laboratory techniques. Other techniques, such as optical methods (e.g., spectroscopic) are costly and have limited use. Further techniques include electro-chemical sensors that are able to provide real-time or near real-time bacteria assessment.

The control implications of such delays (or due to an unknown level of bacteria) might be that processes are run excessively conservative (e.g., high temperatures, colder temperatures, longer cooking time, higher retort temperatures, frequent washdowns, anti-microbials added, and so forth) to insure low bacterial levels. Periodically product samples may be taken and analyzed in the laboratory to help insure the process keeps the bacteria below threshold levels. It can also be very difficult to change an established or approved manufacturing process for food and pharmaceutical products. A lengthy procedure is often needed to establish the validity and biological safety of a modified process.

SUMMARY

The following presents a simplified summary in order to provide a basic understanding of some aspects of the subject disclosure. This summary is not an extensive overview and it is not intended to identify key or critical elements of all aspects nor delineate the scope of any or all aspects. The sole purpose of this summary is to present some concepts of one or more aspects in a simplified form as a prelude to the more detailed description that is presented later.

An aspect relates to a system that facilitates accuracy in a process affected by microbial agents. The system comprises a detection component configured to directly or indirectly monitor a microbiological species present in a product of the process. The process includes product information and metadata associated with the process. Also included in the system is a biological representation of the microbial agents included in the process. The biological representation is defined with respect to the process representation and the micro-biological species present and is configured to predict bacterial levels. Also included in the system is an adjustment component configured to dynamically modify at least a portion of the process based in part upon the predicted bacterial levels.

Another aspect relates to a method for microbial monitoring and prediction. The method comprises determining a bacterial level in a process by placement of sensors at various stages within the process and predicting a future bacterial level by simulation of the process and simulation of bacterial growth within the simulated process. The method also comprises selectively modifying at least one parameter in the process as a function of the future bacterial level to achieve an improvement to a future product condition or product state.

Yet another aspect relates to a system comprising a first sensor located at a first stage of the process and a second sensor located at a second stage of the process. The first sensor and the second sensor are configured to capture bacteria levels within the process. The system also comprises a process representation configured to simulate the process and a biological representation configured to predict a bacteria level based on the captured bacteria levels. Also included in the system is an adjustment component configured to dynamically modify at least a portion of the process based in part upon a definition of the biological representation. The adjustment component is further configured to evaluate a quality constraint, an energy parameter, or both the quality constraint and the energy parameter before modifying the portion of the process to improve a product, the process, or to achieve one or more business objectives.

To the accomplishment of the foregoing and related ends, one or more aspects comprise features hereinafter fully described. The following description and annexed drawings set forth in detail certain illustrative features of one or more aspects. These features are indicative, however, of but a few of various ways in which principles of various aspects may be employed. Other advantages and novel features will become apparent from the following detailed description when considered in conjunction with the drawings and the disclosed aspects are intended to include all such aspects and their equivalents.

DETAILED DESCRIPTION

Various aspects are now described with reference to the drawings. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing these aspects.

Figure 1:
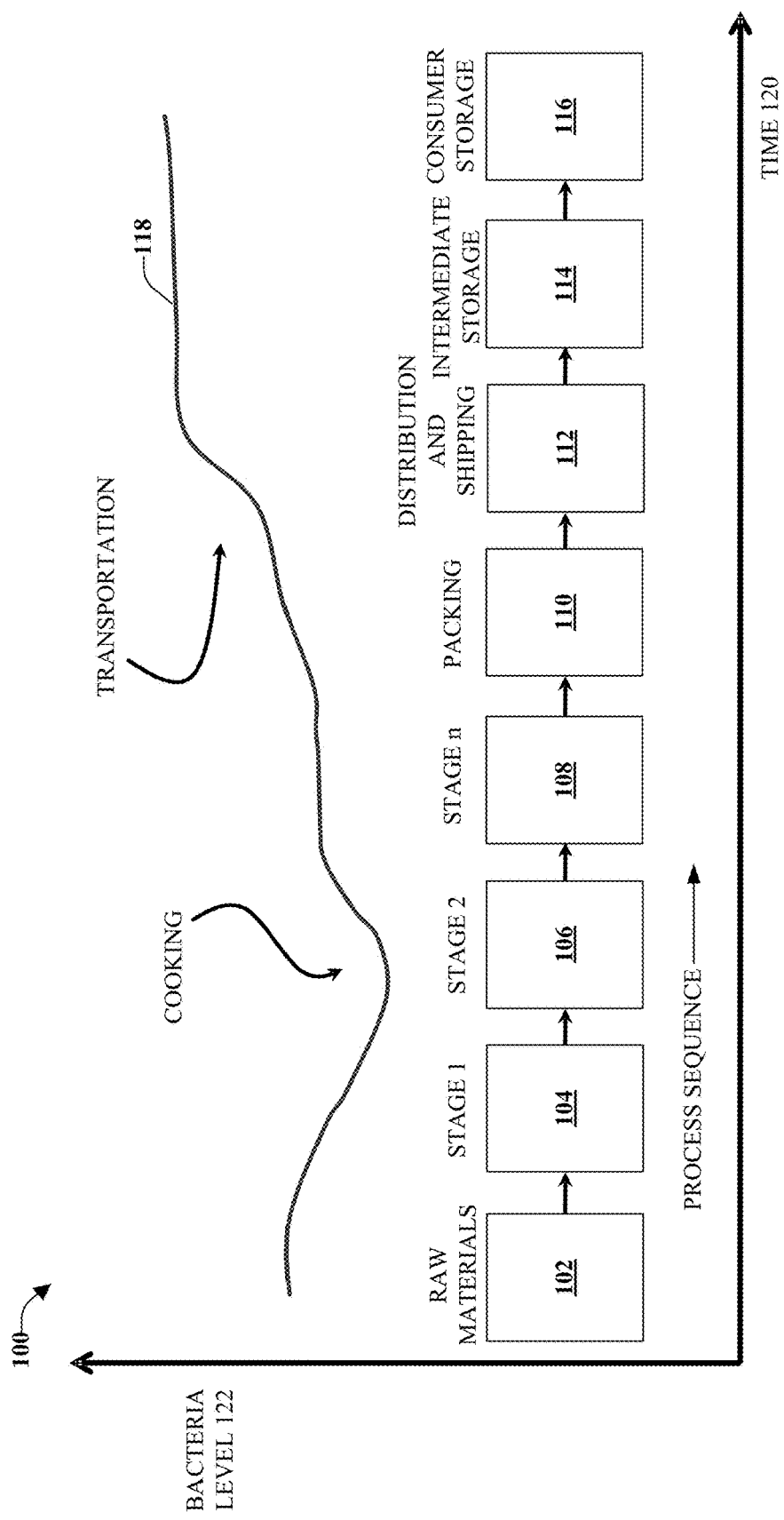
FIG. 1 illustrates a representative process, according to an aspect.

Turning now to the figures, FIG. 1 illustrates a representative process 100, according to an aspect. This figure shows representative steps that might occur in a typical manufacturing process. The steps, while illustrated as a sequential process, may be looped back to earlier steps, may be repeated, may exist as a tree or network of connected steps, and/or may be arranged in many other orders of events or as parallel activities that may or may not be combined in subsequent process steps. Further, the sequence of steps in FIG. 1 is shown for illustrative purposes only. As illustrated, raw materials 102 can be altered, such as in various stages, illustrated as Stage 1 104, Stage 2 106, through Stage n 108, where n is an integer. Raw materials may be altered such as by cleaning, washing, cooking, slicing, coring, blanching, baking, braising, freezing, mixing, blending, kneading, whipping, stirring, extruding, forming, portioning, rolling, cutting, or peeling, for example. The altered materials can be combined and packaged 110 for distribution and shipping 112. The materials might be stored (e.g., in intermediate storage 114), such as in a retail store or distribution center, for example. A consumer, after purchasing the material might store (e.g., in consumer storage 116) the product for later consumption.

Bacterial levels are illustrated by the representative plot 118, where time 120 is represented along the horizontal axis and bacterial level 122 (e.g., culture counts) is represented along the vertical axis. The bacteria levels in representative plot 118 may represent the level (e.g., culture counts) of a particular species, a collection of species, or an aggregate level of all, or substantially all, bacteria species present. As shown by the plot 118, throughout the process, bacteria levels change. It should be noted that not all bacterial levels are measured in every step of the process. Unmeasured bacterial levels may be estimated based on knowledge of bacteria and bacteria characteristics (e.g., species, quantity of bacteria, metabolic rate) and environment (e.g., nutrients present, mixing levels, pH, temperature, times, and environment/air characteristics). For example, bacteria level is expected to decrease during cooking at a specific elevated temperature for a specific amount of time. By knowing the initial bacteria level and the decrease in bacteria that is expected due to a specific cooking regimen, the output bacterial level may be estimated.

In accordance with some aspects, the bacteria state of the input products (e.g., raw materials 102) or ingredients (e.g., from a supplier) can affect the cost to produce a product and/or can affect product quality and product variability. For example, there is a cost associated with an increased level of input product bacteria. The one or more disclosed aspects can predict the cost impact before the product is made or the ingredient is used or even before the raw material is purchased or before the raw material is accepted as received goods by the food manufacturer. For example, bacteria levels in a raw material input may be mapped to the model of the manufacturing process and, thereby, may determine the requirement for longer cooking times (and greater energy consumption), a rescheduled process to use the material before a particular time/day, more frequent laboratory testing, and/or more frequent washdowns. In accordance with some aspects, the model can suggest recovering these incremental costs due to microbial content from the supplier.

According to some aspects, plant performance (e.g., quality, throughput, cost to make, profit, and so forth) can be predicted from the raw material. For example, the disclosed aspects can perform such predication based on a biological state of the input products. Additionally, the disclosed aspects can be optimized to perform the prediction for each unique set of input materials, according to an aspect.

Figure 2:
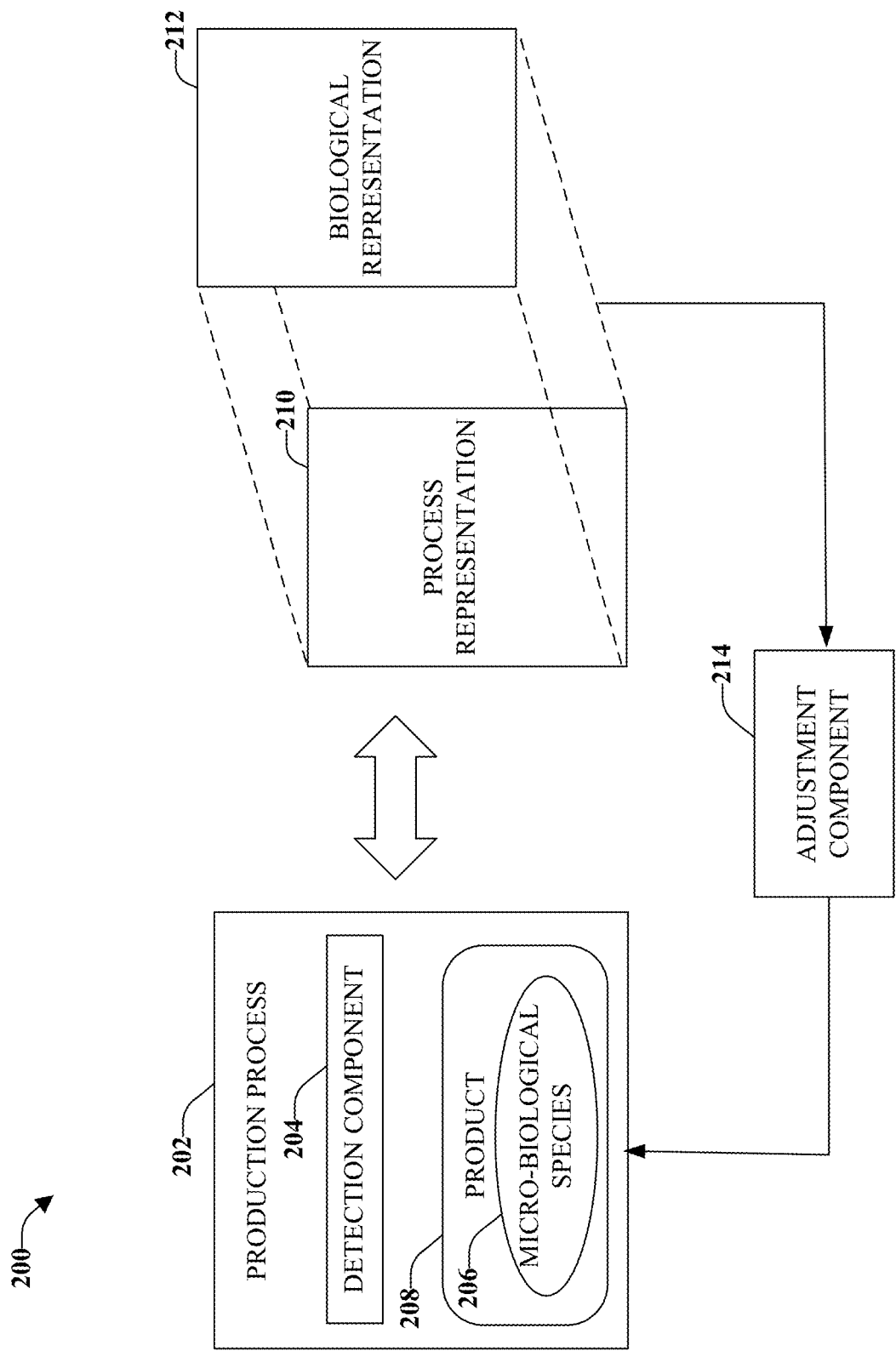
FIG. 2 illustrates a high-level overview of an example system that utilizes microbial monitoring and prediction, according to an aspect.

FIG. 2 illustrates a high-level overview of an example system 200 that utilizes microbial monitoring and prediction, according to an aspect. A motivation for process changes or control parameter changes in accordance with various aspects disclosed herein may include insuring bacteria levels are below an allowable threshold for a current process or insuring acceptable bacteria levels at a subsequent step or time in the future. The resultant bacteria levels following a prescribed change in the process configuration and/or process control changes can be compared to predicted bacteria levels. The prediction methods can be altered as needed to provide for more accurate forecasting of bacteria levels in the future.

The use of modeling and prediction tools can provide a foundation for dynamic process improvement. For example, various control and operational scenarios can be automatically generated and evaluated prior to making any change to the physical manufacturing process. When an improved set of control and operational changes have been identified, a change in the actual manufacturing process may be initiated. For example, the identification of control and operational changes can be performed through repeated and iterative simulation, which can be automatically conducted. The changes should correspond to the improved control scenario evaluated. Finally, various machinery and process configurations, operating conditions, and control techniques can be evaluated to explore the potential benefits of various machinery designs, equipment configurations, and sensing and control options. The improved configuration can be the basis for designing an improved process design that meets (or exceeds or optimizes) processing requirements and that can be readily monitored and controlled in an efficient manner.

System 200 can be utilized in a production process, such as a bioprocess (e.g., fermentation) and/or a process that includes material (or product) that has a limited shelf life wherein the material deteriorates over time and/or includes a product that can be affected by microbial agents. Food product alteration can include a change in chemistry such as a change in pH, change in bacteria count, release of gases, change in density, change in texture, change in viscosity, release of toxic chemicals, changes in color, taste, and odor among others. A few examples of such products include food (such as processed meats, tomato based items, dairy based items, meat, fish, fresh produce, spices and seasonings, beverages, and so on), water, cosmetics, and pharmaceuticals (e.g., antibiotics). Examples of production processes include a meat packing plant, a grocery store, a concession stand, a water purification or processing plant, a beverage plant, a food packaging plant, a food distribution center, product transportation and storage, a cosmetic manufacturing facility, a pharmaceutical plant, a medical facility, a bio-fuels plant, an algae growth and algae processing plant, and others.

System 200 is configured to utilize sensed bacterial information at substantially the same time as a model (e.g., mathematical equation (s), neural net model, analytical approximation, statistical model, analog simulation model, discrete event simulation model, empirical model, or graphical model) of bacterial growth and a model (e.g., representation) for the production process. In such a manner, system 200 can provide information related to an operating strategy (including diagnostic abilities and design abilities) and control parameters. Thus, system 200 can assist operators (or automatically implement one or more actions) to improve process steps and process control parameters and/or the process configuration, sequencing, or scheduling within the production process. The information provided by system 200 can assist in providing a more efficient production of a high quality product and a safe product that contains acceptable levels of bacteria.

In accordance with some aspects, the actions can be linked to optimizing clean in place (CIP) or complete washdowns, which might be required by company policies, United States Food and Drug Administration (FDA), or United States Department of Agriculture (USDA) rules. System 200 can recommend (or automatically implement) what to clean, when to clean, how to clean, how long to clean, chemicals to use in cleaning, and can confirm proper cleaning when the line is restarted (e.g., from sensor information).

Figure 3:
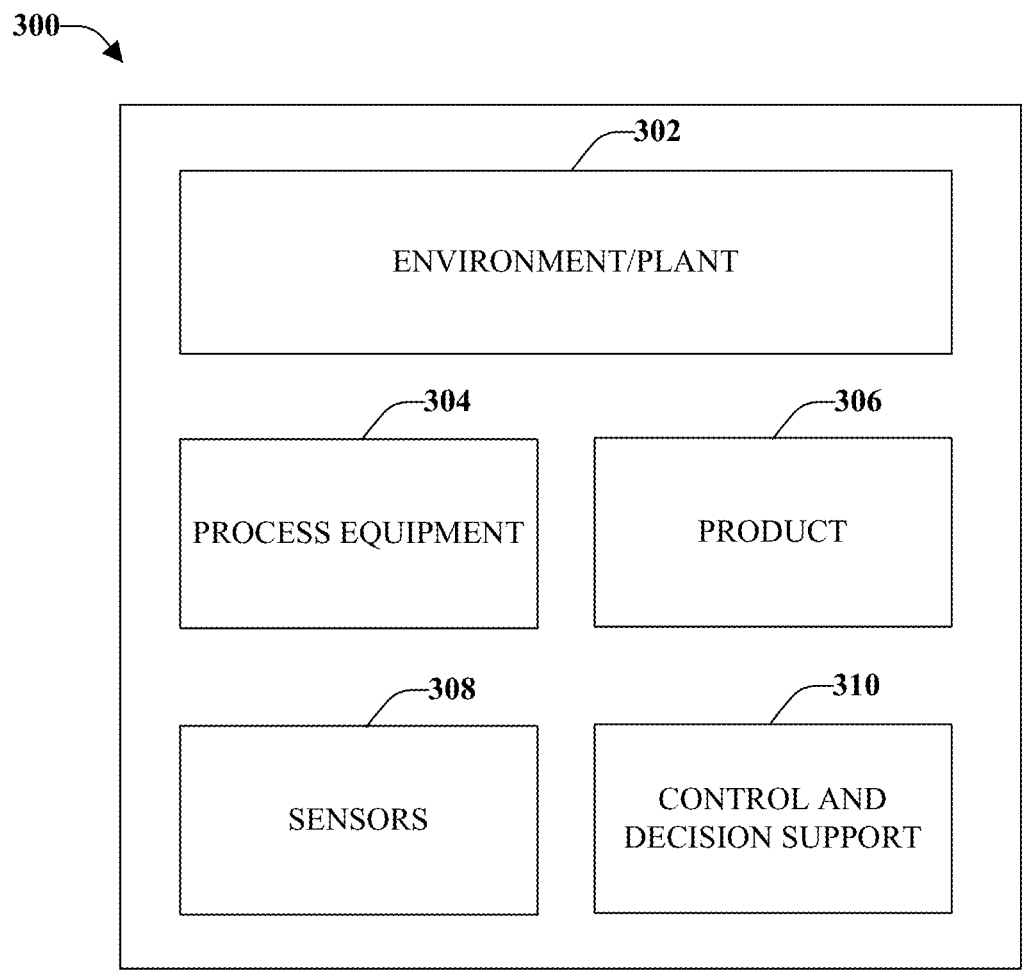
FIG. 3 illustrates an example production process, according to an aspect.

System 200 includes a process that is affected, at least somewhere in the process, by microbial agents (e.g., production process 202). FIG. 3 illustrates an example production process 300, according to an aspect. For example, the production process 300 can comprise an environment or plant 302. The production process 300 also comprises process equipment 304 and product 306. Further, the production process 300 can include one or more sensors 308 and/or control and decision support 310.

In accordance with some aspects, the one or more sensors 308 can determine a bacteria state of a product 306 or of process equipment 304 through various means. For example, the sensor(s) can determine the bacteria state directly, on-line. In another example, the sensors(s) can determine the bacteria state utilizing actual, on-line measurements, and/or off-line measurements (e.g., using established testing protocols). In another example, the sensor(s) can utilize indirect estimation (e.g., measure pH and associate a change with the metabolic level of bacteria). Further, the sensors(s) can employ model-based means (using an analytic model of bacteria growth) for one or more species and use this at substantially the same time as sensor input. In a further example, sensor fusion can be utilized, wherein two or more sensors are employed and readings are combined to estimate a new level of a parameter (e.g., estimate the presence of a particular bacteria type and growth rate based on a sensed change in fluid chemistry) and/or to improve the accuracy of a measurement (e.g., increased accuracy of a bacteria estimate based on a change in the amount of nutrient sensed). In further detail, sensor fusion can estimate and/or predict bacterial levels for bacteria that cannot be directly measured. Sensor fusion can provide for estimating an unmeasured quantity and/or for improving the accuracy of a measured parameter.

In a further example, a neural network estimator for real-time bio-assessment is utilized (e.g., employ an autoassociative neural network that has been trained using at-line or off-line laboratory data). In accordance with some aspects, a combination of these techniques can be utilized. In accordance with some aspects, the use of autoassociative neural networks can be utilized to confirm proper sensor readings and/or to estimate other readings on-line. In accordance with some aspects, the autoassociative neural network may synthesize the value of what would otherwise be returned from a defective sensor. The autoassociative neural networks can execute in real-time on a controller and/or can be trained off-line using laboratory analysis results and/or stored sensor data.

With reference again to FIG. 2, in some cases, the production process 202 may potentially be affected somewhere in the process, such as in the case of aseptic processes where no bacteria should be present but may inadvertently be introduced into the process. The production process 202 can include various production machinery, such as process equipment, (e.g., ovens, freezer, mixers, grillers, retorts, cookers, peelers, slicers, wash tanks, storage tanks, pumps, presses, conveyors, and so forth). The production process 202 can also comprise programmable logic controllers (PLCs), switches, sensors, servers, databases, or any other suitable software/device that can be used in connection with a production system that processes food or other items that have a shelf life and/or that can be damaged by (or improved by) bacterial levels (e.g., pharmaceuticals, cosmetics, beverages, neutraceuticals, and so forth).

As illustrated, production process 202 comprises at least one detection component 204 configured to directly or indirectly monitor micro-biological species 206 present in a product 208 of the production process 202. Although only one product 208 is illustrated, it should be understood that there can be multiple products within the process. In an example, the detection component 204 can comprise or can be associated with one or more sensors that are configured to detect, classify, and/or quantify various micro-biological species that may be present in the product (or other locations and/or on machinery within production process 202). The one or more sensors should be able to detect the presence of bacteria, classify the bacteria type, and/or estimate the concentration of the bacteria or estimate the viability and/or growth rate of the bacteria (e.g., utilizing information on bacteria species, nutrients present, pH level, and expected time and temperature). In accordance with some aspects, bacteria detection may be performed by directly detecting the bacteria such as with a species-selective enzyme on an electro-chemical sensor, a molecular imprinted polymer coating on a sensor, using polymerase chain reaction (PCR), or optically (e.g., spectroscopically). According to some aspects, the sensor may be implemented on-line for routine or periodic in situ monitoring. Alternatively or additionally, sensing may be performed at-line, such by using a hand-held bacteria sensor immersed in a product sample extracted from the process line. Alternatively, the sensing may be performed off-line in a laboratory setting using a bio-sensing protocol or bio-sensor and the laboratory results communicated to a computer or programmable controller employing a computer-resident bacteria model.

Also included in system 200 is a process representation 210 (e.g., process model) that models the production process 202. The process representation model is an abstraction of the actual production process that captures the salient features effecting the bacteria state, product chemical and physical changes, process equipment, operation, and temporal aspects of the process. Process representation 210 is configured to describe the sequence of times, process conditions (e.g., temperatures, pressures, chemical additions, mixing, and so on) along with possible changes in the process flow and process parameters that may be altered. Based on process constraints and bacteria growth predictions, suitable (or more desirable) future process conditions can be prescribed to help to insure bacteria levels stay below critical levels while maximizing production output, machinery utilization, revenue generation, or uninterrupted run time or minimizing energy use. Furthermore, the process may be optimized in real-time and changes in the control process initiated automatically. Lastly, multiple parameters (e.g., bacteria level and production rate) may be optimized using the biological model in conjunction with established multi-objective optimization and/or dynamic optimization techniques. For example, running a sub-process a few degrees hotter and for a slightly longer time may stall bacteria growth enough to permit the process to continue operation longer before needing to shut down for cleaning and wash down.

System 200 also includes a biological model or biological representation 212 and/or a bio-chemical representation of the multiple microbial species along with their unique nutrient needs and metabolic ranges that might be present in the production process 202. The biological representation 212 can be defined with respect to the process representation 210 and can be used at substantially the same time as (or superimposed on) the process representation 210, the bacteria species, colony size and distribution, and location (e.g., in a pipe, mixing tank, valve, and so forth). The biological representation 212 can be a bacteria growth model that can predict or anticipate a future amount of bacteria that might be present in the product, machinery, or other item being monitored. The prediction can be a time-based measure and can be based on a given initial nutrient level as well as temperature, mixing rate, pH, homogeneity of the material, and an initial bacterial level of the product (or other item) and ingredients present. The prediction can also be based on the expected environmental conditions (e.g., temperature profile, pressure, humidity, acidity, and so forth), which can be derived, in part, from the process representation 210.

In accordance with some aspects, the sensor captures the bacteria level at one or more stages in the process and the biological representation predicts the amount of bacteria expected to be present in the product in one or more other stages in the process. According to some aspects, the sensor detects micro-biological species present in a product of the process. Additionally or alternatively, the sensor classifies and quantifies a micro-biological species present in a product of the process, or predicts the type, quantity, and growth rate of a micro-biological species present.

In many cases, it is not practical to place bio-sensors in every machine or location of interest in the manufacturing plant (or other process) due to cost, accessibility, or location. According to some aspects, the biological representation 212 is utilized to fill in gaps or stages in the production process 202 where there are no sensors. For example, sensors can be placed at critical points in the production process 202 and for other areas within the production process 202, the biological representation 212 estimates the bacterial growth with a model of the bacterial growth. This can provide an estimate of the expected bacterial levels at various times in the future under specific processing and environmental assumptions. A set of possible or potentially useful processing conditions can be established and the impact on microbial growth can be estimated using the biological growth model. The results of the modeling and analysis can be used to identify a preferred, superior, or optimum set of future processing conditions that can result in the best processing conditions to be enacted with the controller.

In accordance with some aspects, the biological representation 212 can be an analytical model that describes the change in bacteria levels in future time steps based on starting conditions (e.g., bacteria count, nutrient levels, environment, pH, and so on) and expected or possible future changes in the environment (e.g., storage at elevated temperature for a specific time period). The biological representation 212 can also include a model of the metabolism of the bacteria and the expected changes in the product chemistry (e.g., nutrient depletion, pH changes, and so on). For example, the bacteria, *lactobacillus planterum*, may be preset in a tomato-based product. This bacteria converts sugars and other materials to acetic acid and lactic acid (among others). This change in chemistry affects the bacteria growth rate, the product quality, pH, and the future chemical and biological changes in the product. Modeling these changes under current (and possible future scenarios) permits selecting a feasible future control strategy and process conditions and can permit optimizing production output with acceptable bacteria levels. The model can generate a family of time-based trajectories of bacteria levels based on expected changes in the process and expected environment. For example, the biological representation can define a bacteria level trajectory and the adjustment component can control the process to track an optimal bacteria trajectory.

Figure 4:
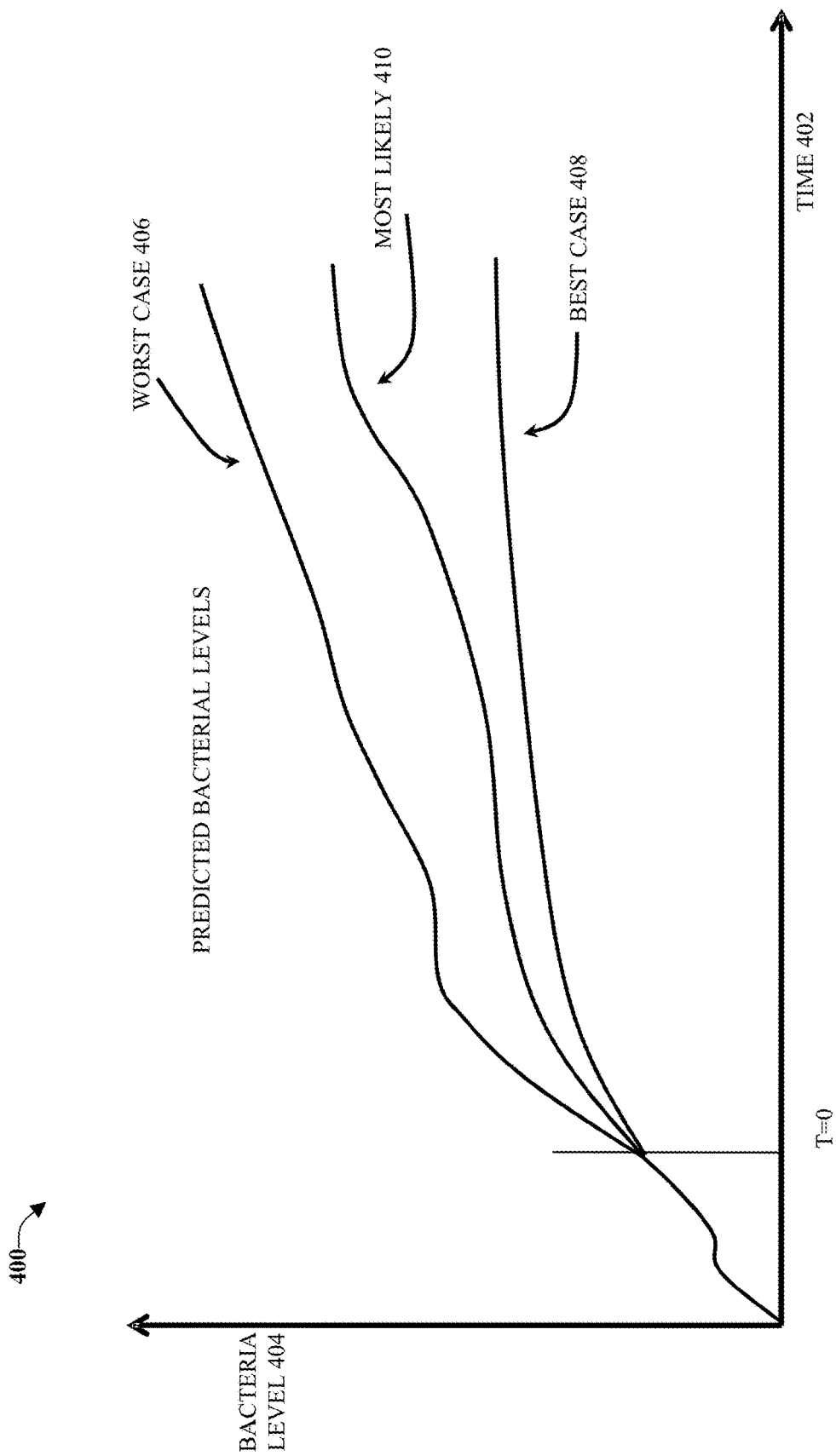
FIG. 4 illustrates an exemplary plot of predicted bacteria levels, according to an aspect.

The accuracy of these estimates might decrease over time and a range of expected bacteria levels and most likely bacteria level can be estimated as shown in FIG. 4, which illustrates an exemplary plot 400 of predicted bacteria levels. Time 402 is represented along the horizontal axis and bacterial level 404 is represented along the vertical axis. As shown by the plot 400, an upper level estimate for bacteria levels (curve 406), a lower level estimate for bacterial levels (curve 408), and a most likely estimate for bacterial levels (curve 410) is shown. If the objective is to reduce or minimize the bacteria levels, then the scenario shown by curve 406 represents a worst-case scenario and curve 408 represents a best case scenario. If the objective is to insure an adequate level of bacteria (e.g., for making pharmaceuticals or yogurt), then curve 406 may represent a more desirable bacteria level than curve 408. However, in each case, the model of bacterial growth coupled with the process model permits estimating the expected future bacteria level as a function of the process and variations that may be made in the process to achieve target bacterial levels, more desirable bacteria levels, or optimum bacteria levels.

In accordance with some aspects, the sensing information is derived indirectly based on other parameters that are measured (e.g., pH, sugar content, chemical parameters, viscosity, color, and so on). Based on the parameter measured, the bacteria level can be inferred (using the process representation 210 and/or biological representation 212). The future expected levels of bacteria can be predicted at specific locations in the process. These may be locations where sensors are not installed, according to an aspect.

An adjustment and control component 214 is configured to dynamically modify at least a portion of the control sequencing or schedule of the production process 202, in part, upon the definition of the biological representation 212. In some aspects, the adjustment component is further configured to dynamically modify the portion of the process to minimize cleaning cycles or to improve cleaning effectiveness. For example, adjustment component 214 is configured to improve the product or the process as a function of the biological representation 212. Adjustment component 214 can modify the portion of the production process 202 in real-time (or in near real-time). In accordance with some aspects, adjustment component 214 can adjust one or more parameters (e.g., temperature, speed at which the product moves through the process, and so on) of the production process 202 as a function of the definition of the biological representation. The one or more adjustments can be made to meet a process or operation constraint, which can include a constraint on bacteria levels and chemistry changes due to bacteria metabolism. In accordance with some aspects, the adjustments made by adjustment component 214 can be based on one or more objective functions (e.g., reduce scrap by 3%, increase production by 15%, bacteria below a threshold level, minimum energy use, and so on).

In an example, a bacteria level of incoming material might be captured and, based on the bacteria level, it might be determined that the incoming material should be processed immediately and/or should be processed at a higher temperature and/or a faster speed. Later in the process, the bacteria level of the material (in its then current form) might be captured again (e.g., feedback loop) and another change to the process can be made (e.g., production speed reduced to a normal rate if the bacteria level at the current stage is appropriate for the product). Furthermore, the measured bacteria level information can be combined with process conditions experienced by the raw material to adaptively change and improve the accuracy of predicting future bacteria levels. For example, feedback can be utilized to adaptively and automatically improve the model (e.g., adaptive learning). For example, processing a raw material with a known starting bacteria level according to a known set of process conditions can result in a specific level of bacteria that can be measured. The measured change in bacteria may be associated with a particular set of processing steps and stored in a computer (e.g., storage media). Subsequent batches of raw material with a known bacteria level can have the final bacteria levels estimated for each set of possible processing conditions before processing begins. Changes in process conditions can be made upstream to help obtain a final, more desirable bacteria level.

According to some aspects, adjustment component 214 can be utilized to dynamically modify one or more changes in manufacturing. Such changes can include changes to control parameters, process parameters (e.g., temperature), changes in equipment, different ingredients, changes to the sequence of processing steps, changes to a schedule of products to be made, changes to environmental parameters (e.g., plant humidity, plant temperatures), or combinations thereof.

According to some aspects, system 200 can be configured to link in-plant bio-tracking and bio-modeling with tracking and tracing (e.g., the actual location of the product). Thus, the in-process information can be used to help confirm if a food safety problem exists and can help isolate the food products affected. Further, this can help assist in a determination of the root cause of the contamination. For example, detection component 204 can directly or indirectly obtain location information for products and can be utilized with the detected micro-biological species present in the process. Based on the location information and the detected micro-biological species present, one or more modifications can be made within the process, including future modifications.

In accordance with some aspects, adjustment component 214 is a classical linear programming (LP) optimization, a multi-objective optimization procedure, or other optimization technique (e.g., gradient search) that determines a future operating process that can optimize objective function(s) and/or process constraint(s).

In accordance with some aspects, system 200 includes at least one autonomous agent within the process. The at least one autonomous agent communicates and autonomously implements an action in an upstream stage within the process. The at least one autonomous agent accesses the representation of the process and the biological representation to implement the action.

In accordance with some aspects, the autonomous agent corresponds to a process stage, process step, or a group of processes. The at least one autonomous agent predicts the bacteria state of material leaving the process stage. The predicted value can be used to change the processing before the stage is complete and/or the predicted value at the end of the stage is communicated to other upstream and/or downstream process agents.

According to some aspects, the system 200 comprises at least two autonomous agents within the process. Each of the at least two autonomous agents correspond to different segments of the product being processed, processing stages, or processing elements. For example, a product material agent can be configured to predict its bacteria levels and communicate the bacteria levels to a control and adjustment component to help insure proper bacteria levels. The agent representing the product being processed can also communicate and share information and negotiate with other agents representing portions of the product being manufactured (e.g., upstream and/or downstream segments of products).

In another aspect, the two (or more) autonomous agents represent different segments of the product being processed and processing stages or processing elements. The agents can predict bacteria levels and communicate among each other and with other agents. Further, the agents can collaborate and negotiate with each other to establish a more desirable or more optimal future processing condition. In some aspects, the agents can initiate the preferred change in processing, monitor the resultant change experienced, and/or modify models, controllers, tables, and so forth, to adaptively change operations such that future operation can be improved with respect to current operations.

Figure 5:
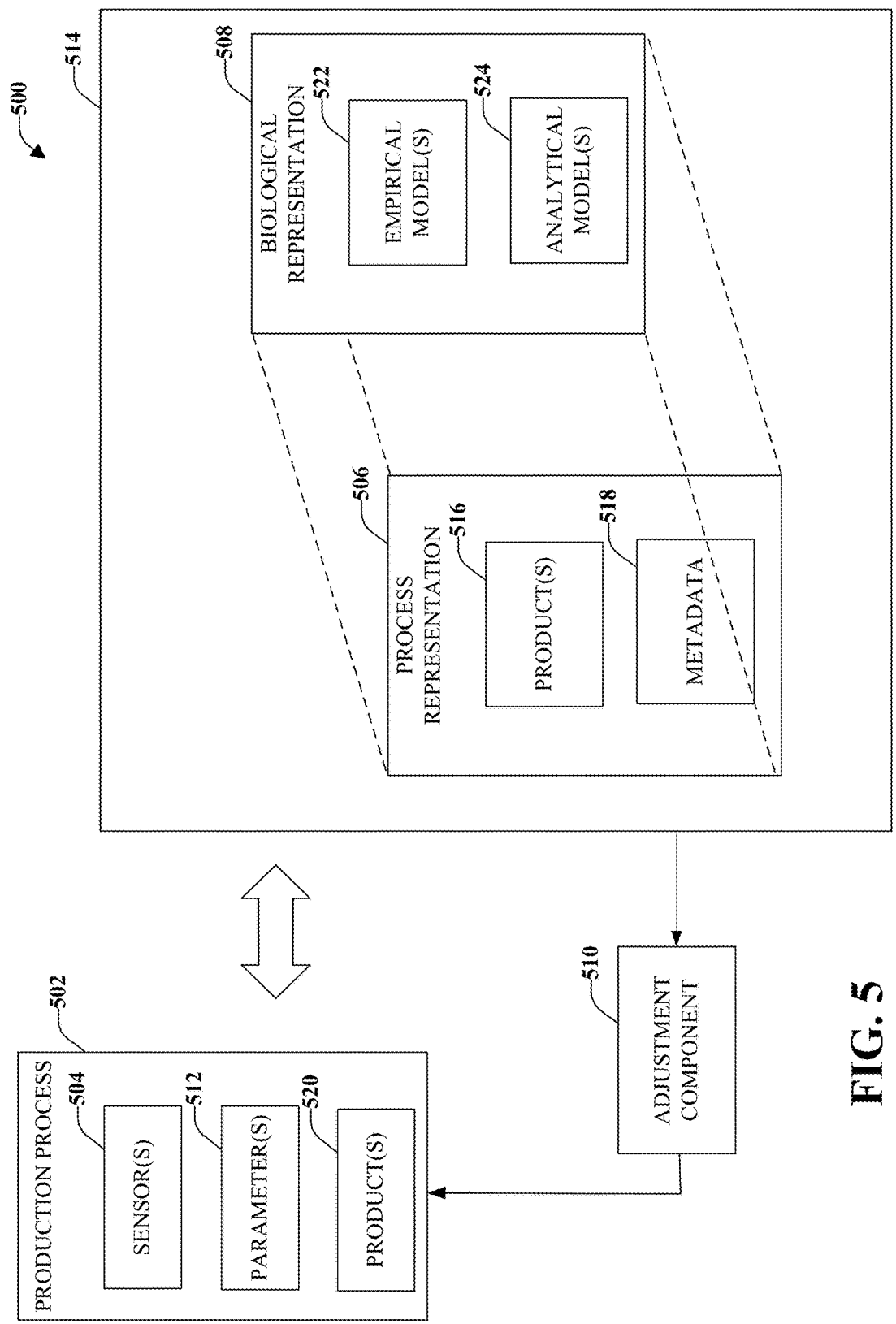
FIG. 5 illustrates a system that facilitates accuracy in a process affected by microbial agents, according to an aspect.

FIG. 5 illustrates a system 500 that facilitates accuracy in a process affected by microbial agents, according to an aspect. The term "facilitates accuracy" can include one or more of a multitude of processing objectives. Examples of processing objectives include efficiency, optimization, energy efficiency, lowest cost product, longest equipment lifetime, maximum runtime, longer interval between shutdown and clean, shortest time for cleaning, maximum throughput, most consistent product, lowest life cycle, as well as other objectives or a combination of these objectives (e.g., using multi-objective optimization techniques).

System 500 can mitigate an amount of scrap by dynamically changing process conditions in response to sensed and predicted bacteria levels. System 500 can also mitigate product spoilage and the amount of unsafe or unacceptable product being produced. System 500 can also predict a bacterial level further downstream in the process, which can save time as well as costs that would be incurred as opposed to waiting until the process is finished and then determining the amount of bacteria present (and maybe scrapping the entire product batch). The predicted bacteria levels can be used to alter downstream processing conditions and times to help insure acceptable bacteria levels.

In accordance with some aspects, product quality, safety, and/or reliability can be improved. For example, if changes are made downstream, a benefit can be improved product quality. If changes are made upstream, a benefit may be to avoid more costly or limited downstream remedial action (in the future) and/or to avoid scrap in the future. The prescribed change may be to a current stage, one or more upstream stages, and/or one or more downstream stages.

System 500 comprises a production process 502 that comprises at least one component, illustrated as a sensor 504, configured to directly or indirectly determine a bacteria level within the system 500. For example, the sensor 504 can directly detect or estimate the presence of bacteria. The presence may be an assessment that bacteria is present, determination of the type or species of bacteria(s) present, the quantity of bacteria present, whether the bacteria is living or dead, the metabolic rate or growth of the bacteria, or any combination of these bacteria related features. For example, a change in pH may be used to estimate the bio-reactions that have occurred and provide a basis for estimating the amount of bacteria present and the expected increase in bacteria at some time in the future.

In accordance with some aspects, the component can indirectly determine a bacterial level within the process. For example, the bacterial level can be determined indirectly by monitoring other process parameters and performing calculations to determine the bacterial level. In another example, the bacterial level can be obtained from an outside laboratory (e.g., microbiology laboratory) or an in-house laboratory.

System 500 also comprises a process representation 506 and a biological representation 508, wherein the biological representation 508 is defined with respect to the process representation 506. In accordance with some aspects, the biological representation can be a computer-based representation of the characteristics of the bacteria that can emulate or simulate the biological activity of the bacteria. However, according to some aspects, there can be other biological representations that do not permit simulating biological activity.

Also included in system 500 is an adjustment component 510 that utilizes information derived from the process representation 506 and the biological representation 508 and modifies one or more parameters 512 within the production process 502. In accordance with some aspects, the modification of a portion of the production process 502 can include reconfiguration of the process. In some aspects, the modification can include dynamically changing an operation of one or more controllers. Further, the modification can include using the information to define a more efficient processing configuration of the production process 502.

According to various aspects, the predicted bacterial levels may remain for a period of time after the product has been packaged and shipped (e.g., a future level). Based on the predicted bacterial levels, the shelf life of the product can be estimated. If the shelf life is undesirable, then process conditions may be implemented (or changed) such that a more desirable or extended shelf life is obtained.

Figure 6:
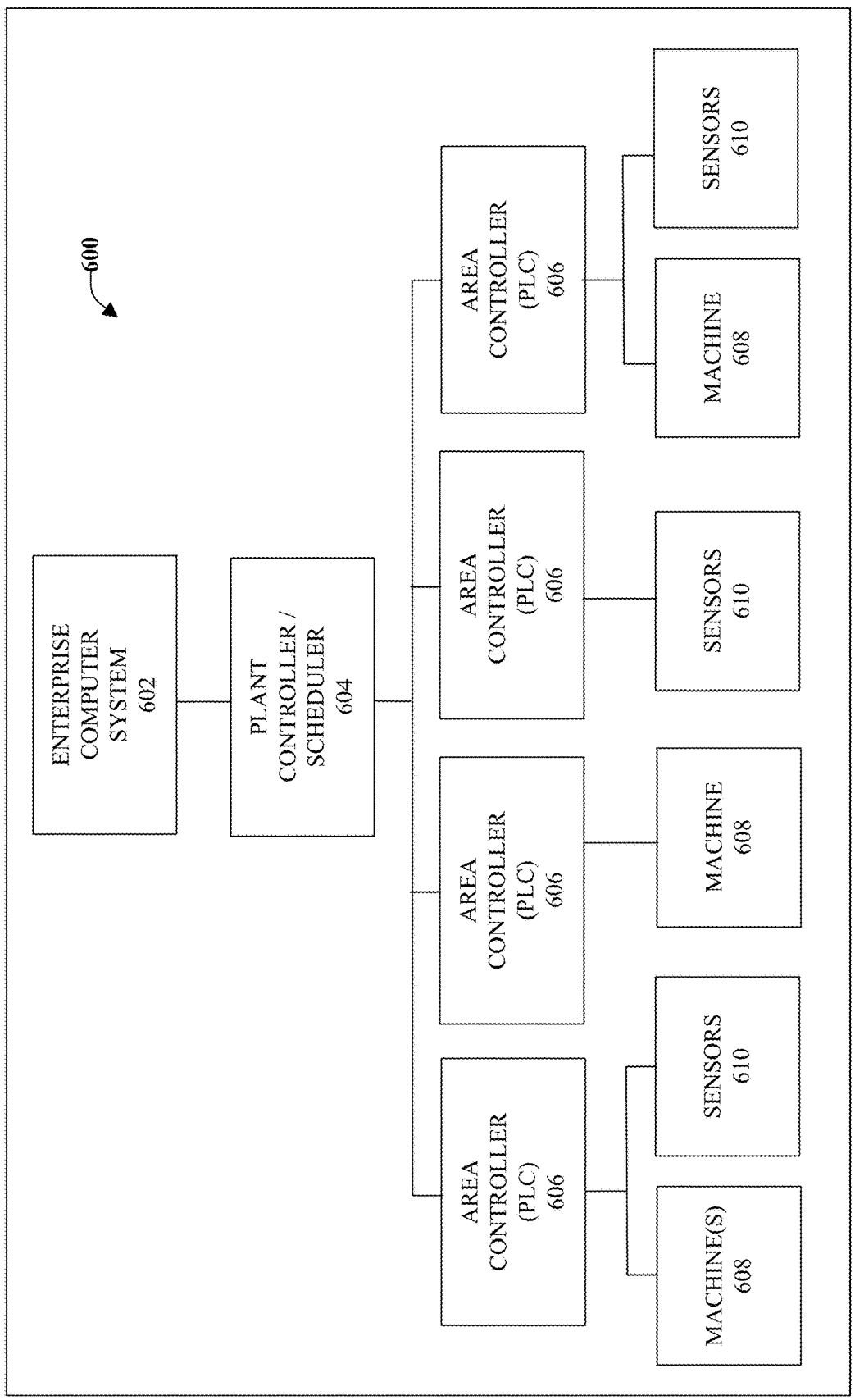
FIG. 6 illustrates an exemplary organization information and manufacturing system hierarchy, according to an aspect.

Process representation 506 and biological representation 508 can be included in an automation platform 514. According to some aspects, adjustment component 510 can be included, at least partially, within automation platform 514. However, in some aspects, the system elements, such as controls, models, and so forth, may be distributed among multiple processors and/or geographically distributed. According to some aspects, production process 502 utilizes at least a portion of automation platform 514, wherein automation platform 514 is a controller, such as a personal computer (PC), programmable logic controller (PLC), microcontroller, single-board computer (SBC), or embedded computer, that can adjust one or more parameters 512 to meet operating constraints to achieve the best results possible. The controller can process the control logic for all the relevant plant production processes that produce the product along with controller coordination logic. The controller may be a linear controller, adaptive controller, model-based controller, predictive controller, state-space controller, neural net controller, or other controller topology and may include process (or plant) models and may dynamically change the process based on the sensed or predicted process state. The controllers can be a hierarchy of controllers of a network of controllers, as shown by the exemplary organization information and manufacturing system hierarchy 600 of FIG. 6. In the example hierarchy 600, an enterprise computer system 602 controls a plant controller/scheduler 604, which controls a multitude of area controllers 606 (e.g., PLC), which can control one or more machines 608 and/or sensors 610.

For example, bacteria levels may be monitored (continuously, periodically, at defined intervals, at undefined intervals, upon request, or at other times) and feedback can be provided to the controller. Other sensors can provide additional information on the process conditions relevant either directly or indirectly to bacterial growth. Such information can include temperature, viscosity, sugar content, pressure, aeration level, pH, or antimicrobial agent concentration, for example. The controller can also provide actual or observed process conditions (e.g., temperatures, times, and so on) that may be correlated with bacterial levels and subsequent product conditions to support adaptive process modeling and self-learning systems. Based on the error between the predicted bacteria levels and the observed or measured levels, the model may be manually or automatically altered to improve the prediction accuracy. A self-learning model can adapt to changes in bacteria species, metabolic rate, and environmental changes without having to explicitly encode all process details and to permit the model to respond to un-modeled disturbances. In accordance with some aspects, deviations from observed conditions to conditions estimated by the model can serve as a diagnostic tool and can signal a fault in a sensor, process control problems, recipe problem, clean in place problem, and/or the presence of a new bacteria species.

With reference again to FIG. 5, the process representation 506 can be utilized at a first stage in the production process 502 to predict or anticipate the condition of the product in a second (or subsequent) stage in the production process 502. The predication can be based on a future control action that is expected to be taken in the second (or subsequent) stage in the production process 502.

In accordance with some aspects, boundary constraints are utilized to link the biological condition of a product existing in one stage and entering another stage. Alternatively, an estimate of an upstream biological condition can be revised based on a downstream calculated and/or measured biological state.

Process representation 506 is an abstraction or model of the real, physical production process 502 that manufactures a product, such as a food product, pharmaceutical product, or other production process. Operating in parallel with the computer-based process representation 506 is a biological representation 508, which is an abstraction or model of the biological activity that occurs in the real, physical production process 502. Together, the two abstractions or models, comprising process representation 506 and biological representation 508, can operate in parallel to provide a suitably accurate dynamic model of the actual physical bio-chemical operation occurring in the actual production process 502.

Process representation 506 (or process model) can simulate the production process 502 and can comprise product information 516 and metadata 518 associated with the product. For example, process representation 506 is configured to represent or model products (e.g., food items or ingredients, material used in the production of cosmetics, and so forth) and represent or model production equipment and also model or simulate the time-based interaction between these elements (e.g., product recipe) within the production process 502. The modeled product(s) can be monitored to determine an expected time and location of the product as the product moves through the production process 502. For example, the product might be located on a storage shelf before the product is used in production and for an amount of time x. In another example, the product might be located in an oven (for cooking), in a mixer (for mixing with other ingredients), in a freezer, and so forth. The location of the product(s) along with the expected processing times and transfers and wait times can be utilized to predict a future time and location for the product. Further, the location and time the product(s) is utilized to determine whether a sensed bacteria level conforms to an expected and/or predicted bacteria level. If the bacterial level is too high (or too low) adjustments to the one or more parameters 512 can be made by adjustment and control component 510.

In accordance with some aspects, process representation 506 can employ metadata 518 associated with the production process 502 as well as software objects that are employed to represent the production process 502. The metadata 518 can include data that identifies products 516 within the process representation 506 (and products 520 within the production process 502) and the location of such products. The metadata 518 can further include definitions of industrial processes that occur within the production process 502. It should be understood that the process representation 506 is not limited to a specific manner of representing the production process 502 and any suitable manner of representation is contemplated by the disclosed aspects.

In accordance with some aspects, the one or more sensors 504 can determine a level of bacteria at various stages within the production process 502 and inform the automation platform 514 (or another component) of the detected levels. The adjustment component 510 can thereafter analyze the process representation 506 to automatically re-configure the machinery or change control or processing conditions (e.g., adjust a cook temperature, speed up a conveyor belt, and so on) in accordance with the metadata 518 that describes the production process 502. In accordance with some aspects, metadata 518 associated with the product and/or machinery (e.g., the bacterial level or other information) can be manually entered by an operator and/or user of the automation platform 514. Metadata can also be derived from process control information, process feedback data, operator input, or transmitted from a remote computer (e.g., enterprise level computer, master recipe database, or from an OEM product performance database).

In accordance with some aspects, the adjustment component 510 can automatically generate user interfaces in accordance with the metadata 518 as well as interfaces that facilitate data exchange between the production process 502 and the process representation 506. For example, the metadata 518 can include information relating to a particular user of the automation platform 514 (or controller), such as user identity, user privileges, operator skill level, user activities, and other suitable information that can be utilized in connection with creating an appropriate user interface. Therefore, a customized user interface can be automatically generated by the adjustment component 510.

According to some aspects, the adjustment component 510 can be employed to automatically structure databases (or the like) for use when collecting data relating to the production process 502. For example, the production process 502 that includes a plurality of sensors 504 can generate a substantial amount of data relating to manufacturing system(s)/process(es). The system 500 enables an operator or user to request data collected from a particular machine, set of machines, stage within the process, and/or product and the adjustment component 510 automatically generates a database structure that collects data in accordance with the request. The collected data can be employed in future representations of the process and/or bacteria, according to an aspect. The captured data may be analyzed using established data mining techniques.

Biological representation 508 can be based on at least one empirical model 522 and/or at least one analytical model 524. The empirical model 522 can be based on laboratory conditions and testing, pilot plant studies, published growth rates and historical plant data among others. In accordance with some aspects, the empirical model 522 can be utilized with the process representation 506 to provide design abilities, wherein the adjustment component is configured to design a production facility, design a production process, or alter an existing facility or the process as a function of the biological representation 508. For example, a plant to be built or a new production process within an existing building being designed may utilize bio-process model information to optimize the design of the facility and optimize processing steps and control conditions resulting in a optimum production process. The empirical model 522 (or a previously developed analytical model 524) can be utilized to determine the flow of product within the plant and to optimize the design so that costs associated with cleaning processing and/or scrap can be mitigated.

The analytical model 524 can be based on actual production conditions that were previously recorded. For example, on the production floor, samples of product are analyzed to determine the bacteria growth that is present at various stages within the process. There can be in-situ sensors within the process that perform the monitoring (e.g., continuously, periodically, on request, on conditions, or at other times). For example, a change in pH might indicate that lactic acid has built up due to the presence of bacteria in a tomato based product. This information is included in the analytical model 524 in order to predict the occurrence of bacteria in a future product, wherein conditions are the same as (or similar to) the sampled product. The biological representation 508 can be an analytic model, a stochastic model, a model-free estimate (e.g., artificial neural network) or other model types, or a combination of two or more models (e.g., stochastic parametric model).

In accordance with some aspects, an input to the biological representation comprises a comparison of the bacteria level within the process and at least one actual bacterial type and level measured during a future stage of the process. For example, the actual bacteria type and levels encountered in the future (e.g., on a product that has previously undergone processing) is compared to the predicted types and levels. The difference between the predicted values and the actual values can provide a basis for process diagnostics, equipment diagnostics, product contamination, product tampering, or for adaptively changing the model to improve the accuracy of future bacterial predications.

According to some aspects, other models can be utilized. For example, an analytical or statistical model can be a model of the equipment and a model of the product being processed in the equipment. Another type of model that can be utilized is a bio-estimation model using other than sensed parameters, such as chemical sensor input. Other models that can be utilized with the disclosed aspects include statistical models, simulation models, neural network models, empirical models. Further, a combination of the above can be utilized with the disclosed aspects.

In accordance with some aspects, changes made to the production process 502 by adjustment component 510 are analyzed and the result of such changes are fed back to process representation 506 and/or biological representation 508 to dynamically update simulations of the production process 502 and bacteria levels in the production process 502.

The adjustment component 510 analyzes the process representation 506 and the biological representation 508 and re-configures the production process 502 and/or provides recommendations with respect to the production process 502 in accordance to the analysis. In accordance with some aspects, the adjustment component 510 is an intelligent component that re-configures the production process 502, the process representation 506, and/or the biological representation 508 based at least in part upon the metadata 518.

Figure 7:
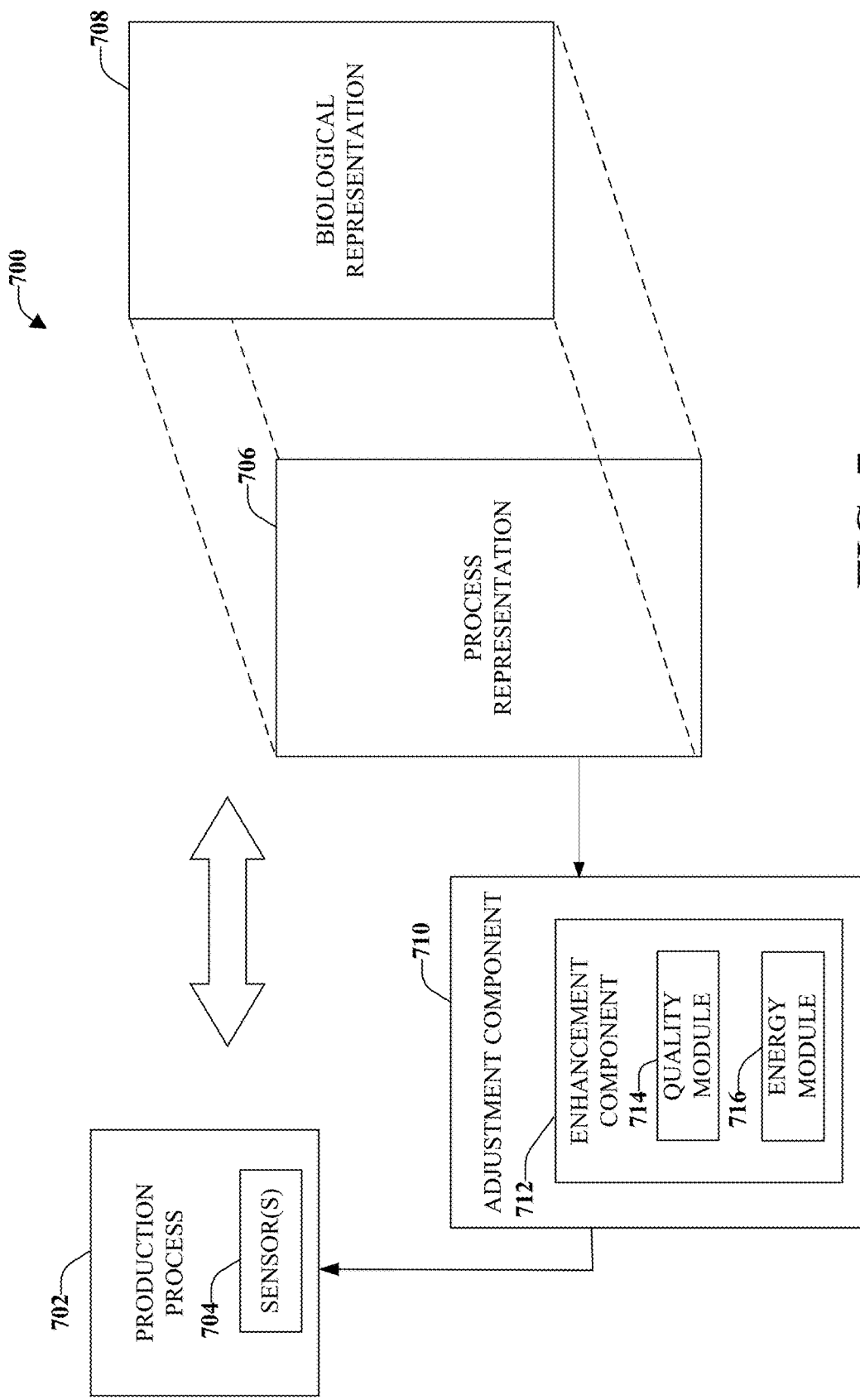
FIG. 7 illustrates a system that dynamically controls a process by monitoring and predicting bacteria levels, according to an aspect.

FIG. 7 illustrates a system 700 that dynamically controls a process by monitoring and predicting bacteria levels, according to an aspect. In accordance with some aspects, system 700 utilizes bio-measurement or bio-estimates and state prediction to implement control alteration. System 700 can automatically change at least one process parameter and/or production schedule based on production model and biological model data, according to an aspect. By changing at least one process parameter, system 700 can attempt to mitigate scrap in response to sensed and predicted bacterial levels. System 700 can also attempt to avoid product spoilage and mitigate unsafe or unacceptable product from being produced. The dynamic control by system 700 can help to keep bacterial levels below critical thresholds. Alternatively, the control can provide a more consistent level of product quality to lower the cost of production (while meeting constraints on quality including bacteria levels) or a combination of objectives (e.g., multi-objective optimization).

System 700 comprises a production process 702 that includes one or more sensors 704 that can directly or indirectly detect the presence and/or level and/or type of bacteria. Also included in system 700 are a process representation 706 and a biological representation 708 that simulate or model various parameters and/or bacteria levels expected to occur within the production process 702. Based on the predicted bacteria levels, an adjustment component 710 can suggest and/or automatically implement at least one change in the production process, if needed. The prescribed changes can include one or more of the following, for example: change in process parameter (e.g., cooking temperature), stirring rate, cooking time, chemical amendment to add and the amount to add, schedule to add amendments, schedule to add ingredients or mixing schedule (e.g., mixing speed and duration of mixing), scheduling of products (e.g., process batch A before batch B) and work-in process, sequencing of production operations, and product routing. The change prescribed is directed at meeting one or more biological constraints while meeting or optimizing one or more business or production parameters, such as cost, throughput, or product quality.

In order to determine whether a change should be implemented, adjustment component 710 can access an enhancement component 712 that is configured to evaluate various efficiencies and goals of the production process 702. Based on the evaluation, adjustment component 710 can implement the action, formulate a different action, or take no action. In accordance with some aspects, enhancement component 712 evaluates an objective, function, and/or one or more constraints on the process as a function of the definition of the biological representation, wherein the adjustment component 710 dynamically modifies the portion of the process as a function of the evaluated objectives and/or constraints.

Enhancement component 712 can comprise a quality module 714 that retains (or has access to) quality parameters. The quality parameters can be maintained in a storage media, database, or in another retrievable format. Some examples of quality parameters can include maintaining a bacteria level above (or below) a certain threshold or within an allowable range at various stages within the production process, keeping a temperature above (or below) or within a range of a certain amount at various production stages, processing material within a certain time limit, and so on. As a function of the quality parameters, it might be determined that a certain action cannot be taken and, therefore, the product might need to be thrown away (e.g., scrapped) instead of taking the recommended action.

Additionally or alternatively, enhancement component 712 can comprise an energy module 716, wherein adjustment component 710 can access energy module 716 to determine whether a particular change should be applied to production process 702. Energy module 716 can retain (or have access to) desired energy parameters, which can include energy usage limitations, target energy usage, actual or predicted energy use, energy cost, energy quality, energy reliability, energy demand-response profile, carbon usage (e.g., negatively impacting carbon credits or carbon footprint), GHG (green house gas emissions), or other energy criteria. The energy parameters can be maintained in a storage media, database, or in another retrievable format. For example, adjustment component 710 might consider implementing an increased temperature during a cooking process and/or extending the cooking process to provide an acceptable bacteria level in the product. Before automatically implementing the action (or before recommending the change) adjustment component 710 accesses energy module 716 and discovers that raising the temperature (or increasing the cooking time) will result in a percentage increase in energy usage that is beyond the desired level. The threshold level may be based on energy cost, equipment limitations, or product chemistry or physical composition changes at elevated temperatures. For example, the expected energy usage may alternatively result in an estimated increase cost of the product that is undesirable and, therefore, the change in production may not be selected for implementation. Thus, in this case, adjustment component 710 might determine that it would be better to scrap the product rather than implement the action that is necessary to decrease (or slow down) the level of bacteria in the product.

In accordance with some aspects, adjustment component 710 can establish and/or receive information related to objective functions (e.g., goals). Based on the objective functions and operating constraints, adjustment component 710 can implement a decision support system that can optimize critical business and/or process performance measures to meet the objective functions.

For example, adjustment component 710 can implement and/or recommend various changes to meet or exceed product safety by monitoring and estimating biological levels. Discrepancies between observed and predicted values may be a potential signal of an inappropriate product and/or process alteration, equipment degradation, equipment malfunction, sensor fault, raw material quality problem, or other production process problem. In accordance with some aspects, the disclosed aspects can be utilized for anomaly detection. For example, the residuals (e.g., differences between observed and predicted values) can be calculated at each step of the process. The residuals, including the trend and rate of change of residuals, can be analyzed and utilized as a diagnostic tool, such as to detect a machine or process fault or equipment degradation, or raw material problem, or a sensor failure, or incorrect processing conditions (e.g., wrong recipe used), or unauthorized product, or process alteration, or tampering, for example. Thus, the adjustment component 710 can be configured to perform algorithm adaptation and/or process diagnostics in response to observed bacterial levels not matching predicted bacterial levels (e.g., analyze residuals).

Figure 8:
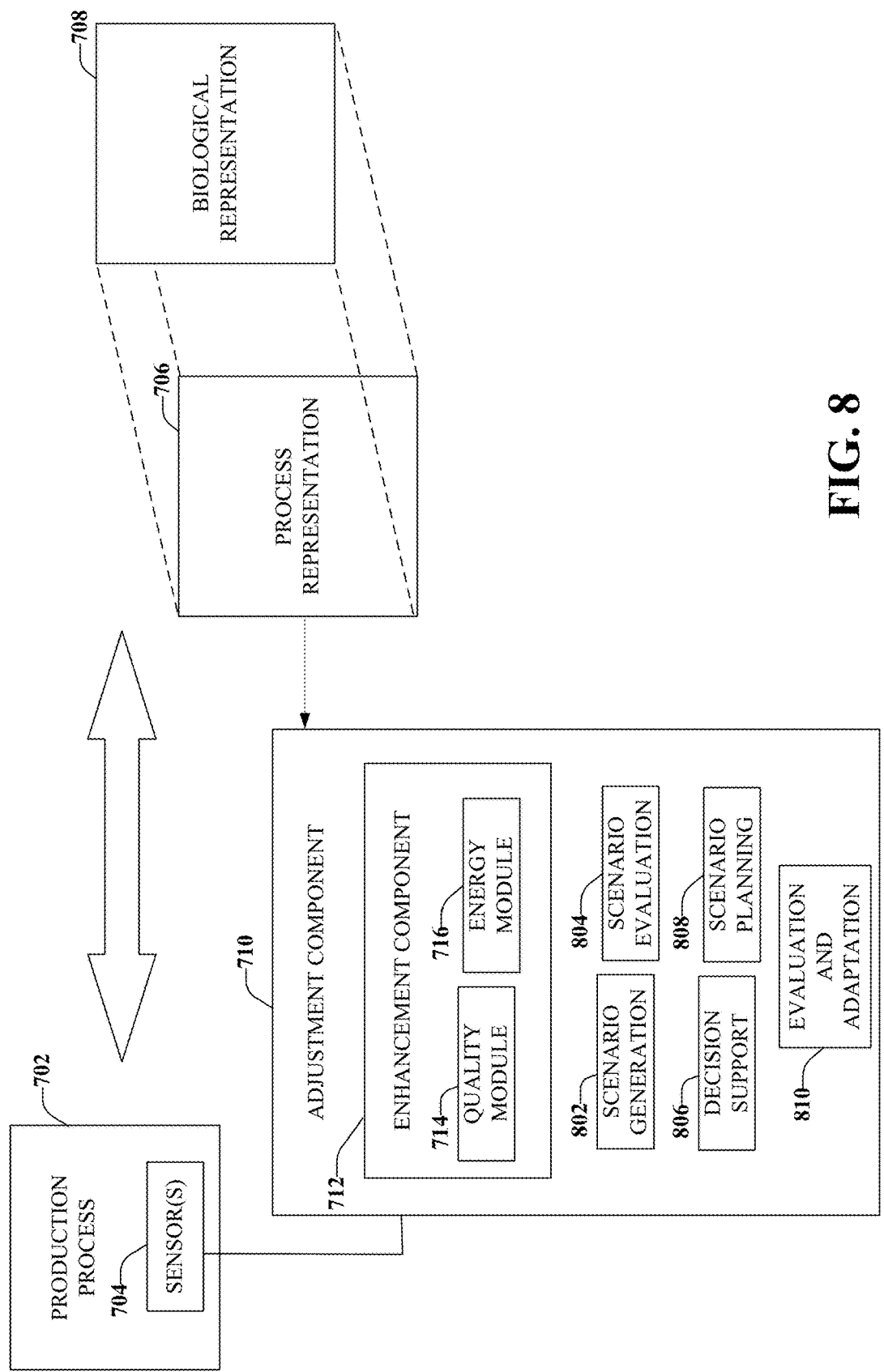
FIG. 8 illustrates another aspect of the adjustment component of FIG. 7, according to an aspect.

The adjustment component 710 can be further extended, as shown in FIG. 8, to include a function for generating a collection of potential future operating states. The adjustment component 710 can evaluate the desirability of the future operating states based on the predicted bio-process state. The adjustment component 710 can then select the best possible future operating condition and generate a series of steps to transition the process from the current (e.g., less desirable) operating state to the new (e.g., more desirable) operating state. The resulting bio-process condition and business impact actually realized from the selected operating scenario can be evaluated and prediction models altered to further improve the prediction accuracy and impact prediction results for subsequent predictions made by the adjustment component 710.

This can be implemented, for example, by utilizing a scenario generation model 802 that is configured to develop a suite of possible, feasible operating conditions that will meet (or exceed) the production objectives. For example, an operating condition can be to run the batch in the cooker longer but at a lower temperature. Another example of an operating condition is to run the batch in the cooker at a hotter temperature but for a shorter time.

An evaluation module 804 can be configured to evaluate each of the operating scenarios generated and can also be configured to determine the biological condition of the system. At substantially the same time (or at a different time), the evaluation module 804 can determine other parameters, such as throughput, energy cost, reliability, quality, risk of failure, and other relevant operational and economic measures. The result of this evaluation can be processed by a decision support module 806. The decision support module 806 can be configured to select the most desirable possible future operating condition based on an established set of measures relating to business performance, product safety, and/or reliability.

The selected future operating scenario may then be used by a scenario planning module 808 that is configured to determine the changes in control and the configuration needed to transition the system from a current operating state to the selected, more desirable future operating state. The control actions may be carried out and can subsequently alter the operation of the process. After the transition is completed, the observed process conditions can be captured by an evaluation and adaptation module 810 that is configured to determine the accuracy of the prediction used to select the current state (e.g., more desirable future operating state). Additionally, the modeling and evaluation modules previously used can be modified (e.g., parameter adjustment or algorithm modification made) to help insure that future, similar conditions encountered will provide a more accurate prediction and evaluation of potential future operating states.

Figure 9:
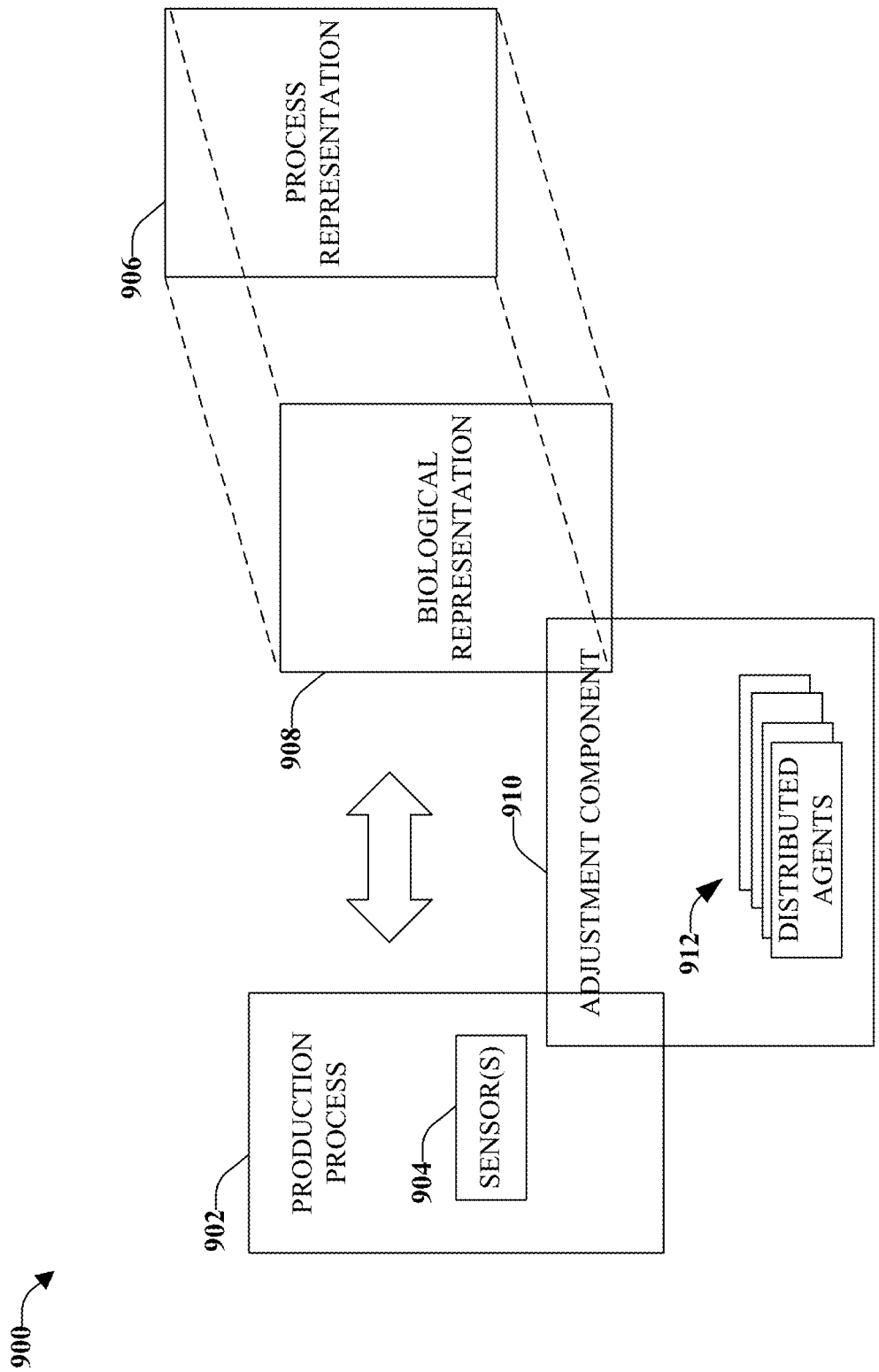
FIG. 9 illustrates a system that utilizes autonomous agents for microbial monitoring and prediction for process improvement, according to an aspect.

FIG. 9 illustrates a system 900 that utilizes autonomous agents (or distributed agents) for microbial monitoring and prediction for process improvement, according to an aspect. Each autonomous agent can represent one or more of a product, a process, or a machine. System 900 is similar to the systems of the above figures and includes a production process 902 that comprises a sensor 904 (or a plurality of sensors) that captures a bacterial level within the production process 902. Alternatively or additionally, process parameters (e.g., temperature, motor current used in a mixer indicating viscosity) and/or other process sensors (e.g., color) may provide information to estimate or approximate the biological state of the system. In accordance with some aspects, a plurality of sensors capture bacterial levels at different stages (or areas) within the production process or different sensors in the same area (e.g., species selective sensor and chemical sensor). Also included in system 900 is a representation of the process (process representation 906) and a biological representation 908 of microbial organisms included in the production process. The biological representation 908 can be defined with respect to the process representation 906 and the captured bacterial level(s).

Also included in system 900 is an adjustment component 910, wherein the adjustment component 910 is included, at least in part, in the production process 902 and the process representation 906 and/or biological representation 908 are included, at least in part, in the adjustment component 910. Adjustment component 910 includes at least two autonomous agents, represented as a multitude of autonomous agents 912. Each autonomous agent can be located in a different stage or area of the production process 902. The autonomous agents may be physically distributed (e.g., residing in different computer-based controllers located in different areas of the manufacturing plant) or may reside in close proximity to each other (e.g., in one computer-based controller or several local computer-based controllers). The autonomous agents 912 (or autonomous agents) can have respective elements (e.g., control) and can exchange information with other autonomous agents and/or other components within system 900 (e.g., adjustment component 910, process representation 906, biological representation 908, sensors 904, and so on). The at least two autonomous agents 912 can communicate and autonomously implement an action within a single stage or across multiple stages either upstream or downstream within the production process 902. To determine whether to implement an action, the autonomous agents 912 can access the process representation 906 and/or the biological representation 908 and information from other system agents.

For example, a first autonomous agent can be located in a first stage of the production process, a second autonomous agent can be located in a second stage of the production process, and a third autonomous agent can be located in a third stage of the production process. The first autonomous agent might sense a bacteria level of a product located in the first stage (or might receive the bacteria level from another entity, such as a sensor). Based on this information, first autonomous agent can communicate with second and/or third autonomous agents and collectively the autonomous agents can establish a preferred change in a downstream process. The downstream agent can initiate the change working through adjustment component 910 that best accommodates the expected bacterial levels from the future incoming process material and communicate the results to other agents when implemented. The agent might adjust one or more parameters in the second and/or third stage or in multiple stages and either upstream and/or downstream to achieve target production conditions, which can include achieving target bacteria levels within each processing state and at the end of the production process, for example.

In view of exemplary systems shown and described above, methods that may be implemented in accordance with the disclosed subject matter, will be better appreciated with reference to various flow charts. While, for purposes of simplicity of explanation, methods are shown and described as a series of blocks, it is to be understood and appreciated that the disclosed aspects are not limited by the number or order of blocks, as some blocks may occur in different orders and/or at substantially the same time with other blocks from what is depicted and described herein. Moreover, not all illustrated blocks may be required to implement methods described herein. It is to be appreciated that functionality associated with blocks may be implemented by software, hardware, a combination thereof or any other suitable means (e.g., device, system, process, component). Additionally, it should be further appreciated that methods disclosed throughout this specification are capable of being stored on an article of manufacture to facilitate transporting and transferring such methods to various devices. Those skilled in the art will understand and appreciate that a method could alternatively be represented as a series of interrelated states or events, such as in a state diagram.

Figure 10:
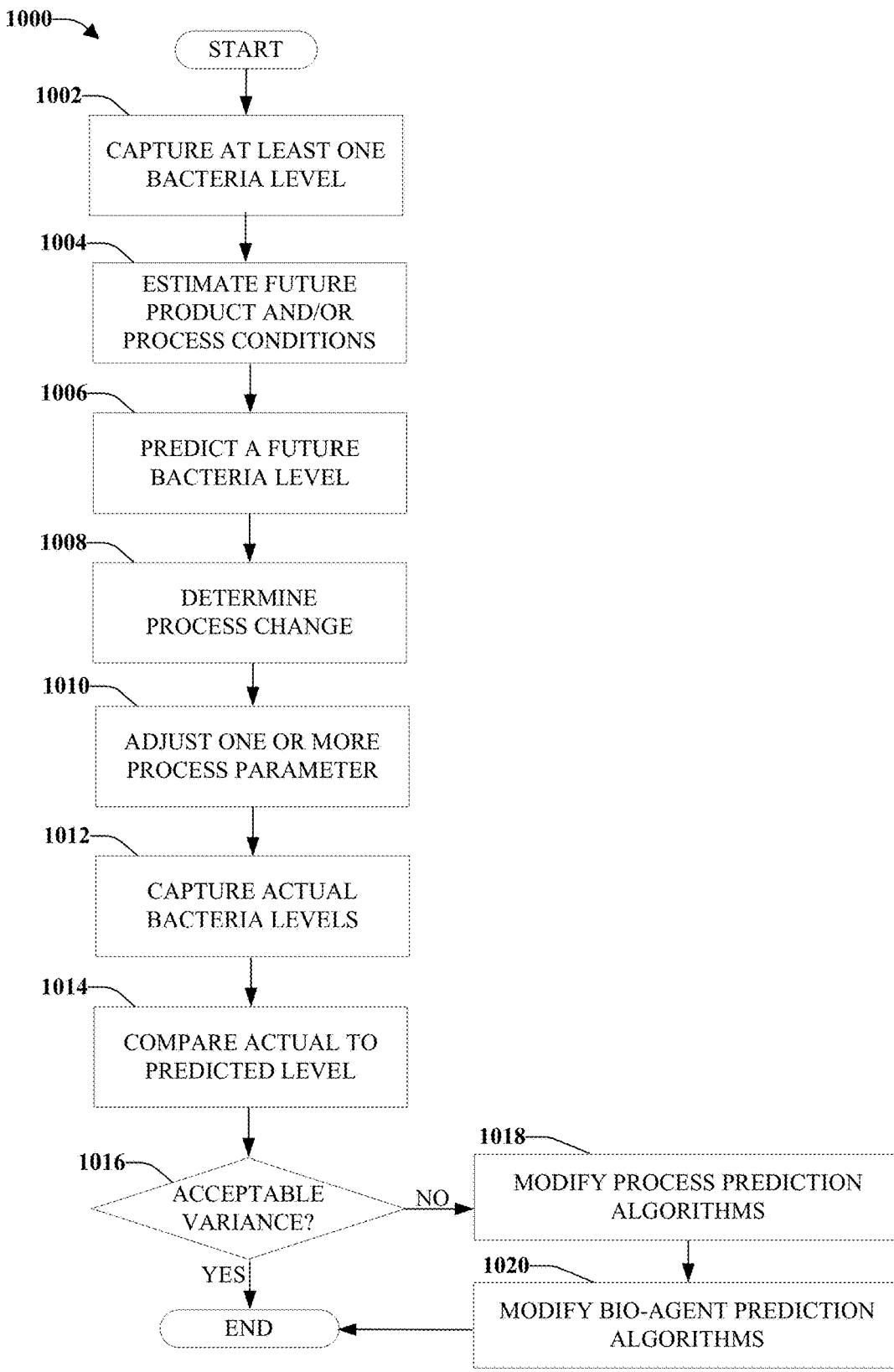
FIG. 10 illustrates a method for microbial monitoring and prediction, according to an aspect.

FIG. 10 illustrates a method 1000 for microbial monitoring and prediction, according to an aspect. In accordance with some aspects, the disclosed aspects can be utilized to isolate problem areas (e.g., unacceptable bio-quality). An example of an operating approach is hypothesis generation and testing. Further, running models capable of characterizing a good or acceptable product or process, as well as separate fault models can be utilized. According to some aspects, the staged model can be iteratively adjusted to fit (or conform to) the data. After any needed adjustments, the model can be analyzed and used to prescribe corrective action (if needed). This information can also be utilized to further train and/or validate the model (e.g., slightly longer cook times might provide a specific biological change in the product).

Method 1000 can dynamically adjust a manufacturing, chemical, or bio-process based on sensed and/or predicted microbial levels in order to more fully enhance the process and product output such as to reduce energy requirements per unit of product produced or to increase production rate or mitigate the risk of unsafe or unacceptable product quality and manage the biological condition of a product and/or process. Method 1000 enables process improvements by using on-line microbiological sensors (or virtual sensors, lab analysis and models, estimated biological condition using process data and/or other non-biological sensor data, and so forth), a model of bacteria growth, prediction algorithms and/or models, a scenario generator module, a decision support module, an evaluation model, a processing planning model, and model adaptation modules at substantially the same time as a dynamic optimizing process controller that effectively integrates the information from the different modules. For example, based on the bacteria level of a current feedstock, a current metabolic rate, an expected growth rate in an expected environment, an optimizing controller may prescribe a higher temperature but shorter duration time blanching process and then direct the material to a high-volume canning line to quickly utilize the material before it becomes unacceptably degraded by bacteria. The bacteria growth and metabolic model coupled with a real-time controller can permit automatically changing the process to help insure maximum production output, minimum waste, minimum energy usage, minimum carbon footprint, and to help insure product quality in spite of changes in upstream bacteria levels or other disturbances that may affect microbial growth. This information can also provide a basis for altering production processes, production equipment, production equipment design, recipes (e.g., target cooking times and temperatures) and production throughput schedules.

Method 1000 starts, at 1002, when a bacterial level in a process is determined. For example, at least one sensor captures bacteria levels within a process. In accordance with some aspects, the method comprises placing sensors at various stages within the process. The sensors can capture the bacterial level directly (e.g., one or more sensors are placed in different areas of a production process) or indirectly, based on sensors that capture other parameters (e.g., pH, viscosity, color, and so on). In addition to sensing bacteria levels, the sensors may also detect micro-biological species present in a product of the process or in (or on) the production machinery (e.g., mixer blades). According to some aspects, the sensors classify and quantify the microbiological species present in the product and at various stages or steps in the process including raw materials and final, packaged products.

In accordance with some aspects, capturing the bacteria levels comprises inserting two or more autonomous agents within the process. The two or more autonomous agents communicate and collaboratively, or individually, determine a change needed in the process and automatically apply a change to the at least one parameter.

At 1004, future product and/or process conditions are estimated and, at 1006, a future bacteria level is predicted as a function of a process model and biological growth rate model and a model of the expected production process and expected environment (e.g., humidity). The diagnostic model can include a process representation and a biological representation, wherein the predicting comprises simulating the process and simulating bacteria growth within the simulated process. The process representation can simulate the production process. In accordance with some aspects, the process representation comprises product information, equipment information (e.g., pipe configuration, pipe bends, pipe welds, valve types, valve locations, heating capacity, mixing rate) and metadata associated with the process. The biological representation can simulate microbial levels in multiple sections included in the process and combine section results. For example, the biological representation can simulate bacteria levels in areas where actual sensors are not present (e.g., model results can fill in gaps between measured sensor values) in the production process. According to some aspects, the biological representation comprises data based on an empirical model of the process. In accordance with some aspects, the biological representation comprises data based on an analytical model, a statistical model, a neural net model, a time series model, and/or other model or prediction method to describe the product's biological evolution in the expected process. At 1008, the predicted bacterial level is compared with the range of desirable bacterial levels and the potential changes in bacterial levels possible. A decision can be made whether to change the process or to continue operating according to the existing control configuration and control parameters. A change may be prescribed for one or more process parameters to achieve a more desirable bacterial level subject to meeting other process and operating constraints.

One or more process parameters are adjusted or selectively modified, at 1010, as a function of the predicted future bacteria level to achieve an improvement to a future product condition or product state. For example, upon making the modification in the process, the actual bacteria levels encountered are determined (e.g., measured directly or indirectly) and compared to the predicted levels. Changes in the process and/or bacteria predication can be modified to improve future prediction accuracy and process performance.

In accordance with some aspects, the one or more process parameters are adjusted based, in part, upon a definition of the biological representation, wherein the biological representation is defined with respect to the process representation and the captured bacteria level. In accordance with some aspects, the one or more process parameters are adjusted to comply with an operating constraint, energy constraint, time constraint, quality constraint, financial constraint, and/or other process limitation or target(s). The change can be presented to a human operator as a recommended operating state or condition or the change may be automatically implemented as a function of an energy criteria and/or a quality parameter or other production or business criteria (e.g., throughput energy usage, revenue generation, and so on).

According to some aspects, the method can include injecting a known stimulus into the process and evaluating a system response to the known stimulus. The known stimulus can be, for example, a brief temperature excursion. The method can also include utilizing the system response to control at least one system element. For example, the system response to a known stimulus can be utilized to validate and improve the modeling, prediction, or an element (or process) of the system.

In accordance with some aspects, the one or more process parameters are automatically adjusted by inserting two or more autonomous agents within the process. The two or more autonomous agents can communicate and collaboratively establish a desirable future operating condition and each can jointly or autonomously implement an action in a downstream or an upstream stage within the process. The two or more autonomous agents can access the process representation and the biological representation to implement the action.

Continuing with FIG. 10, following the initiation of the adjustment of the process parameter and after a suitable delay in order for the change to take effect and for bacteria levels to adapt (i.e., bacteria to alter in type or quantity), at 1012, the resultant bacterial levels and other process parameters are captured and analyzed. The analysis can include confirming that the measured process conditions (e.g., temperature) match the process parameters previously prescribed and implemented and determining the actual bacterial state (e.g., species type, concentration) of the product. The observed and predicted bacterial levels are compared, at 1014.

A determination is made, at 1016, whether the comparison results in an acceptable variance. If the difference between the observed bacterial levels and types are suitably close to the predicted levels ("YES"), no further action is needed. In accordance with some aspects, the entire process, beginning at 1002, may be repeated immediately or at a suitable time in the future.

If the determination, at 1016, is that the difference between the actual observed bacterial levels and the predicted bacterial levels is unacceptable ("NO"), the needed change(s) in the prediction algorithms are determined. Excessive error between observed and predicted bacteria levels may signal the need to alter one or more parameters in an algorithm, update a statistical procedure, replace the prediction algorithm with a new algorithm, provide additional process sensors, improve the characterization of raw material or work-in-process material, and/or implement another change in structure and/or function of the prediction technique(s).

Thus, at 1018, a process prediction algorithm is modified. Alternatively or additionally, at 1020, bio-agent prediction algorithms are modified. The entire process, beginning at 1002, may be repeated immediately or at a suitable time in the future.

Figure 11:
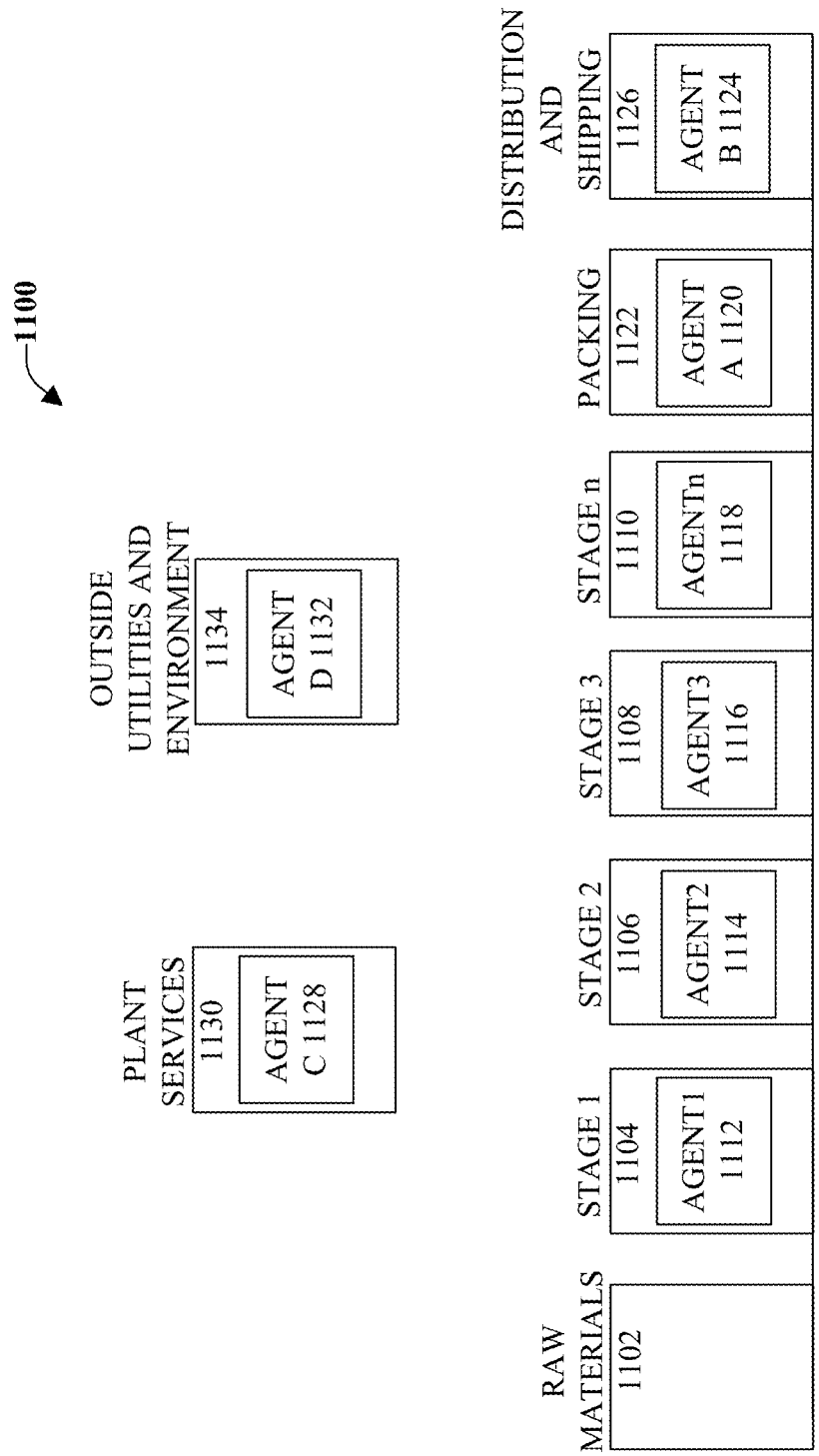
FIG. 11 illustrates an example process that employs autonomous agents, according to an aspect.

FIG. 11 illustrates an example process 1100 that employs autonomous agents, according to an aspect. Raw materials 1102 are processed through various internal process facilities or stages, illustrated as Stage 1 1104, Stage 2 1106, Stage 3 1108, through Stage n 1110, where n is an integer. At each stage, there can be one or more agents, illustrated as Agent 1 1112, Agent 2 1114, Agent 3 1116, and Agent n 1118. Further, an agent (Agent A 1120) can be located in packing area 1122 and another agent (Agent B 1124) can be located in a distribution and shipping area 1126.

Further, there can also be one or more agents (Agent C 1128) representing plant services 1130 and one or more agents (Agent D 1132) representing external or outside utilities and environment 1134, such as electric, gas, water, green house gas emissions (e.g., GHS), and so forth. According to some aspects, a controller, such as a bio-based controller can be configured to interact with at least one internal process facility or an external utility.

In accordance with some aspects, the various systems disclosed herein comprise a first sensor located at a first stage of the process and a second sensor located at a second stage of the process. The first sensor and the second sensor capture bacteria levels within the process. The systems can also include a process representation that simulates the process and a biological representation that predicts a bacterial level based on the captured bacteria levels. Further, the systems can include an adjustment component that dynamically modifies at least a portion of the process based in part upon a definition of the biological representation or estimated bacterial levels based on other non-biological sensor data (e.g., product color) and/or process data (e.g., temperature of product during holding time). Additionally, the adjustment component evaluates one or more product or process objectives or constraints (e.g., evaluates a quality constraint, an energy parameter, or both the quality constraint and the energy parameter) before modifying the portion of the process.

At each stage of the process (e.g., Stage 2 1106), the agent (e.g., Agent 1114) can determine the actual or estimated input bacterial level to its state and determine if the bacteria level is acceptable. If the bacteria level is acceptable, processing will continue as planned. If the incoming material has a bacterial level that is unacceptable, the agent can communicate the problem to an agent that is overseeing the preceding or upstream process (e.g., Agent 1 1112 in Stage 1 1104). The preceding or upstream agent may alter its parameters so that future stage output can change in order to provide a more desirable bacteria level to the downstream stage. Alternatively or additionally, the agents may share other information, such as energy usage, production rate, and processing options and the agents may collaborate or negotiate to determine a mutually preferred bacterial level for material transitioning from one stage to the next (e.g., Stage 1 1104 to Stage 2 1106).

In accordance with some aspects, the agents may also consider the implications for plant services 1130 such as cost, availability, performance, and quality and thereby collaborate with plant services agent(s) (e.g., Agent C 1128) to include considerations for plant services when negotiating to determine a superior or preferred bacterial level between two stages. Similarly, the agents representing processes stages may also consider the implications for outside utilities and environment 1134 and collaborate or negotiate with outside utilities agents (e.g., Agent D 1132) to incorporate information on outside utilities, such as demand response pricing, future energy costs, energy availability, green house gas emissions, and quality, when establishing a superior or preferred bacteria level between two stages.

Carrying the example further, Agent 2 1114 in Stage 2 1106 may estimate the target bacteria level for the product that will be leaving Stage 2 and entering a subsequent stage (e.g., Stage 3 1108) and communicate this to the next stage agent (e.g., Agent 3 1116). Based on the response back from the downstream agent prior to receiving the actual material (e.g., unacceptable bacterial level or excessive cook time required), the upstream agent may alter its current process and thereby alter the bacterial level that the subsequent step actually measures. This can provide a degree of dynamic control and negotiation among process steps that can help avoid having to correct a problem after it occurs or to explicitly define and encode all possible bacteria states and processing conditions.

Figure 12:
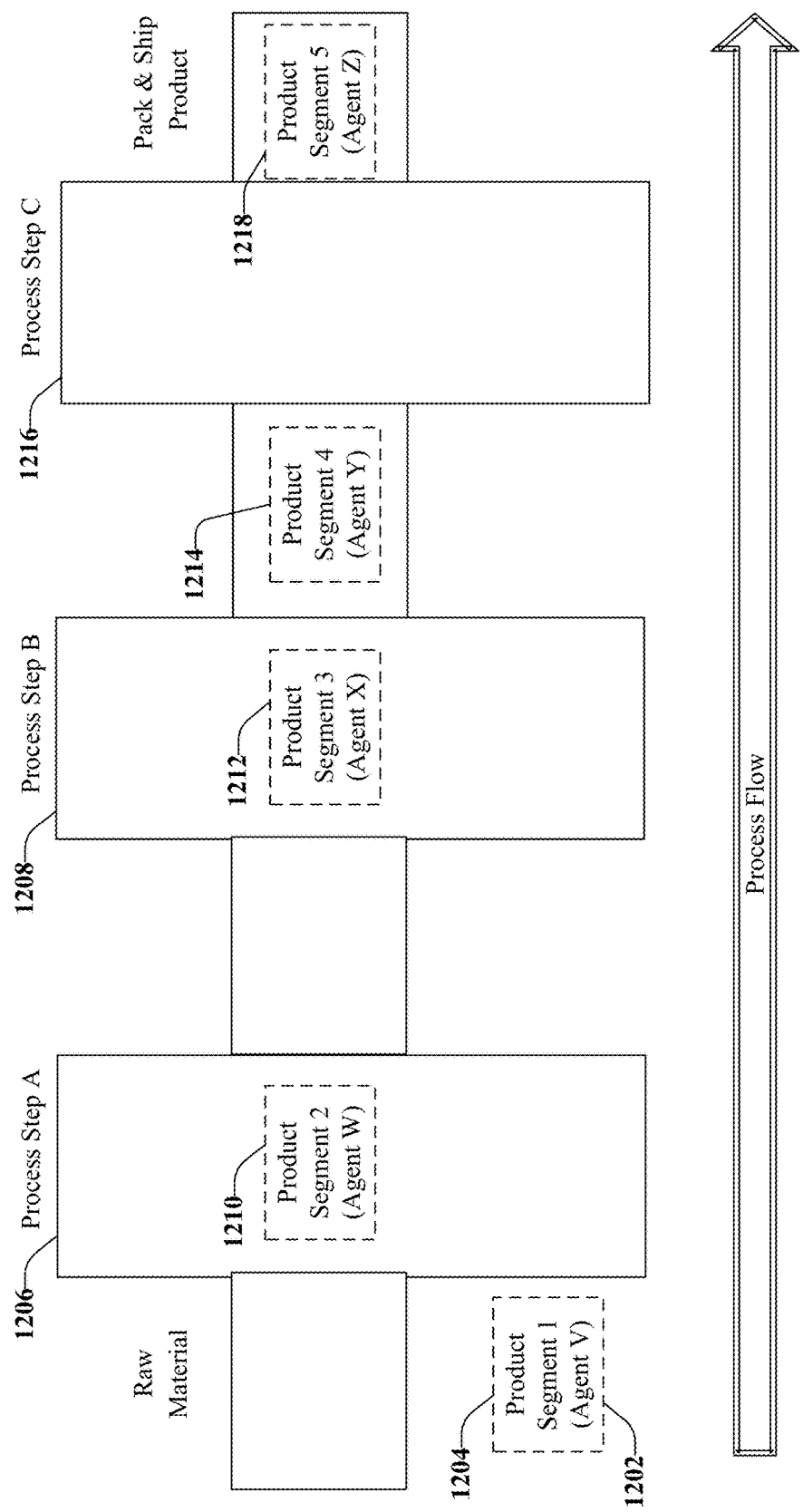
FIG. 12 illustrates the use of agents to monitor and manage a biological state of a process, according to an aspect.

The use of agents to monitor and manage the biological state of a process can be designed and implemented by associating agents to the product being manufactured, as illustrated in FIG. 12. Each product segment or product batch can be represented by an agent. Further, each agent can be translated through the manufacturing process and, through interaction, is processed by various processing steps.

For example Agent V 1202 representing product segment 1 1204 is an abstract representation of the product and includes information such as chemistry, nominal recipe values, and bacteria content. This information travels with the agent (Agent V 1202) as it traverses through the production process. Various processing steps and bacteria sensor readings will change the information associated with Agent V 1202. As Product Segment 1 1204 enters the first processing step, Process Step A 1206, the Agent V 1202 may inform the Process Step A 1206 of the proper or optimal way that Product Segment 1 1204 should be processed. The chemical, physical and biological modifications made to Product Segment 1 1204 can be measured, estimated, sensed, calculated or otherwise determined and retained with Agent V 1202.

As Product Segment 1 1204 exits Processing Step A 1206 and enters Processing Step B 1208, the information is retained and used by the agent to prescribe to Processing Step B 1208 how the material represented by Agent V 1202 is to be processed. The progressive flow of product and information encapsulated by each product segment agent proceeds through the production cycle as shown in FIG. 12

In this figure, examples are shown of product segments that have entered the production process prior to Product Segment 1 1204 arrival and are in various stages of production (i.e. downstream from Product Segment 1 1204). For example, Agent W 1210 represents Product Segment 2 and is in Process Step A 1206. Agent X 1212 represents Product Segment 3 and is in Process Step B 1208. Agent Y 1214 represents Product Segment 4 and is located between Process Step B and Process Step C 1216. Further, Agent Z 1218 represents Product Segment 5 and is located in a packaging area.

Each agent maintains information about its own product segment and communicates to each process step (e.g., piece of process equipment such as a mixer and mixer controller or oven and oven controller) how it should be processed to manage the biological state (and other parameters of the production process). An agent representing one product segment agent may communicate with downstream (or upstream) product segment agents and exchange information on the actual change in bacterial levels encountered or the processing parameters encountered. This can mitigate agents representing product segments that will later enter the same processing step to alter the requested processing parameters as needed to insure appropriate biological levels and chemistry levels and provide a degree of adaptability.

Additionally, an agent may request that portions of a preceding product be retained in a processing step to permit mixing with later product segments and thereby provide a product that will meet bacterial levels, be within quality levels, and/or provide a product with more consistent bacteria or chemical levels. Additionally, both the product segments as shown in FIG. 12 and the process components or process stages may be represented as agents as shown in FIG. 11. This provides a framework for dynamic prediction, collaboration, control, and reconfiguration for optimum processing of biological materials. For example, a product segment agent may communicate processing needs to an agent representing a processing stage yet to be encountered. The processing stage may be unable to accommodate the needed processing parameters. However, through negotiation among different agent processing stages and subsequent reconfiguration, the important processing stage parameters may be satisfied.

Figure 13:
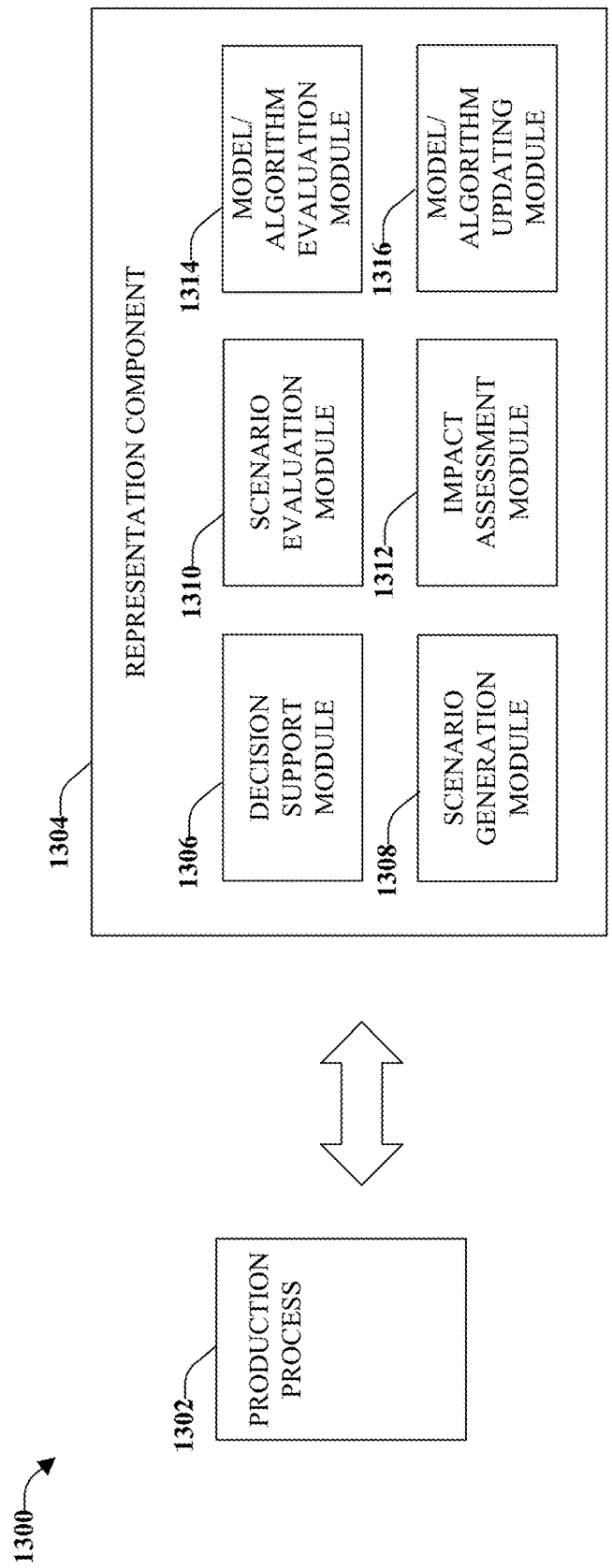
FIG. 13 illustrates another system, according to an aspect.

FIG. 13 illustrates another system 1300, according to an aspect. A production process 1302 can be monitored and/or evaluated in order for one or more models or representations of the process and biological elements within the process to be created by a representation component 1304.

Representation component 1304 can include a decision support module 1306 that is configured to determine whether or not one or more changes should be made at various stages within the production process 1302. For example, a sensor, located within production process 1302, can provide information that is interpreted by decision support module 1306 and, based on the interpretation, decision support module 1306 can recommend one or more changes within the production process 1302 that might be necessary. For example, the change can be an increase in temperature, a decrease in temperature, slowing down the process, speeding up the process, and so forth. The recommended change may be automatically applied to the production process 1302 by altering the set-point or recipe value in a process control computer (e.g., PLC, personal computer, and so forth), for example.

Instead of implementing changes directly within the production process 1302 without knowing if the change is the most desirable change, a scenario generation module 1308 is configured to generate a large suite of possible or potential operating conditions. To generate such changes, the scenario generation module 1308 creates a simulation of the production process 1302 with the one or more changes. A scenario evaluation module 1310 is configured to evaluate whether each potential change in the suite of future potential changes have the desired effect within the simulation of the production process 1302. Each scenario or set of processing conditions can be evaluated by the scenario evaluation module 1310. The scenario evaluation module 1310 can consider the impact of each possible set of operating procedures and apply a set of evaluation criteria, which can result in a measure of desirability (e.g., economic value, desirability metric, throughput value, scrap value) such as by combining one or more product, process, and business metrics.

For example, the scenario generation module is configured to generate multiple potential operating scenarios. The scenario evaluation module is configured to evaluate each of the multiple potential operating scenarios and one of the multiple potential operating scenarios is selected based on a transition plan or another plan appropriate for the facility.

Additionally, an impact assessment module 1312 is configured to ascertain the impact of the one or more changes (e.g., positive, negative, neutral, economic cost, and so forth). For example, the simulation created by scenario generation module 1308 might be to increase an amount of bacteria growth by increasing a temperature by three degrees. However, the impact might be that the energy needed to increase the temperature raises the cost of production by ten percent and, thus, the impact is negative. On the other hand, the increase in temperature might have a positive effect and, although there is a ten percent increase in costs, scrap is reduced by forty percent.

Thus, if the scenario evaluation module 1310 indicates that the impact is positive (or optimal), the change(s) can be automatically implemented within the production process 1302. Alternatively, a suggestion can be provided to an operator to implement the one or more changes to improve the production process 1302. If the impact is negative, one or more other changes can be simulated to determine if a positive impact can occur or whether no changes should be made (e.g., the production process 1302 is operating as efficiently as possible).

Additionally or alternatively, representation component 1304 can include a model/algorithm evaluation module 1314 that is configured to perform prognostics and adaptive learning. For example, a model of the production process 1302 is created and is utilized to predict the future biological condition within a given set of production parameters. If the model results prove to be inaccurate when the product is made (e.g., using feedback information from actual production), the model can be readjusted by a model/algorithm updating module 1316 to improve the prediction accuracy when the same or similar scenario arises in the future.

In accordance with some aspects, the production process 1302 can be interrupted if it is determined that the predicted bacteria levels are in error and do not match measured and/or calculated bacterial levels. According to some aspects, a prescribed production schedule or process can be dynamically amended based on real-time estimates of bacterial levels (as performed by one or more system components that perform the prediction).

In accordance with some aspects, the scenario generation module 1308 can be configured to inject a stimulus to the production process 1302 to perturb (e.g., increase temperature of a holding vat 5 degrees) and assess the condition of the bacteria. This can help validate a model, confirm that sensors are working properly, and can improve the model by accommodating unmodeled disturbances. After the stimulus is injected, the model-predicted changes can be verified (e.g., by impact assessment module 1312) to determine if the changes match the observed change in bacteria levels.

Further to the above aspect, an adjustment component (e.g., adjustment component 214 of FIG. 2) is configured to selectively implement a change in response to a discrepancy between the model-predicted changes to the bacteria level and the observed changes to the bacteria level. If there is a discrepancy, the adjustment component (or an associated component, such as enhancement component 712 of FIG. 7) can be configured to evaluate reasons why there was a discrepancy. For example, the discrepancy can be the result of a malfunctioning sensor or an equipment failure. In this case, the adjustment component can be configured to cause a notification of the failure to be output for correction (either automatic or manual correction). Such corrections can be implemented to mitigate discrepancies in the modeled and sampled bacteria levels.

In another example, the discrepancy can be the result of a change in the product or ingredients (e.g., the model was not updated with the new product or ingredient details) or due to other factors related to the model-predicted changes (e.g., diagnostics, control, or modeling algorithm might be out of calibration or other adjustments might need to be made to the model). In this case, the model can be automatically updated or calibrated to mitigate the discrepancy between observed changes and the model-predicated changes to improve the accuracy of the system.

As discussed above, an aspect relates to system that facilitates accuracy in a process affected by microbial agents. The system includes a detection component configured to directly or indirectly detect micro-biological species present in a product of the process. The process includes product information and metadata associated with the process. The system also includes a biological representation of the microbial agents included in the process. The biological representation is defined with respect to the process and the micro-biological species present and is configured to predict bacteria levels. Also included in the system is an adjustment component configured to dynamically modify at least a portion of the process based in part upon the predicted bacterial levels.

In an implementation, the adjustment component is further configured to dynamically modify the portion of the process to minimize cleaning cycles or to improve cleaning effectiveness. In some implementations, the system includes a bio-based controller configured to interact with at least one of an internal process facility or an external utility or environment.

In another implementation, the biological representation is further configured to define a bacteria level trajectory. Further to this implementation, the adjustment component is configured to control the process to track an improved bacteria trajectory.

According to another implementation, the system includes a scenario generation module configured to generate multiple potential operating scenarios and a scenario evaluation module is configured to evaluate each of the multiple potential operating scenarios, wherein one of the multiple potential operating scenarios is selected based on a transition plan.

In some implementations, the detection component is further configured to directly or indirectly obtain location information for the product, wherein the location is utilized by the adjustment component to dynamically modify the portion of the process. In another implementation, the adjustment component is further configured to adjust one or more process parameters in the process to comply with an operation constraint. In other implementations, the detection component is configured to capture the micro-biological species present at one or more stages in the process and the biological representation predicts an amount of bacteria expected to be present in the product in one or more other stages in the process.

In an implementation, the adjustment component is further configured to design a production facility, design a production process, or alter an existing facility or the process as a function of the biological representation. In another implementation, the detection component is configured to classify and quantify the micro-biological species present in the product of the process, or is configured to predict a type, a quantity, and a growth rate of the micro-biological species present.

In a further implementation, the system includes a scenario generation module configured to inject a known stimulus into the process. The system also includes an impact assessment module configured to verify that model-predicted changes match observed changes in the bacteria levels. Further to this implementation, the adjustment component is configured to selectively implement a change in response to a discrepancy between the model-predicted changes and the observed changes.

In some implementations, an input to the biological representation includes a comparison of the micro-biological species present and at least one actual bacterial type and level measured during a future stage of the process.

According to some implementations, the system includes an autonomous agent within the process that represents one or more of the product, the process, or a machine. The autonomous agent is configured to communicate and implement an action in an upstream stage or a downstream stage within the process and is further configured to access the process and the biological representation to implement the action.

In some implementations, the system includes two autonomous agents that interact to facilitate agent collaboration or agent negotiation. Further to this implementation, each of the two autonomous agents correspond to different segments of the product being processed, processing stages, or processing elements. The two autonomous agents reside in a single computer or each of the two autonomous agents reside in separate controllers.

In some implementations, the adjustment component is further configured to perform algorithm adaptation or process diagnostics in response to observed bacterial levels not matching predicated bacterial levels. In another implementation, the system includes an enhancement component configured to evaluate an objective or a constraint of the process. The adjustment component is configured to dynamically modify the portion of the process as a function of the objective or the constraint.

Another aspect relates to a method for microbial monitoring and prediction. The method includes determining a bacterial level in a process by placement of sensors at various stages within the process and predicting a future bacterial level based on the bacterial level by simulation of the process and simulation of bacteria growth within the simulated process. The method also includes selectively modifying at least one parameter in the process as a function of the future bacterial level to achieve an improvement to a future product condition or product state.

In an implementation, selectively modifying the at least one parameter includes automatically implementing a change in the process based on an energy criteria or a quality parameter.

In some implementations, the method includes injecting a known stimulus into the process and evaluating a system response to the known stimulus. The method can also include performing one of the following: utilizing the system response to control at least one system element or altering a model or recommended change in operations or control.

A further aspect relates to a system that includes a first sensor located at a first stage of a process and a second sensor located at a second stage of the process. The first sensor and the second sensor are configured to capture bacteria levels within the process. The system also includes a process representation configured to simulate the process and a biological representation configured to predict a bacteria level based on the captured bacteria levels. Also included in the system is an adjustment component configured to dynamically modify at least a portion of the process based in part upon a definition of the biological representation and is further configured to evaluate a quality constraint, an energy parameter, or both the quality constraint and the energy parameter before modifying the portion of the process to improve a product, the process, or to achieve one or more business objectives.

Figure 14:
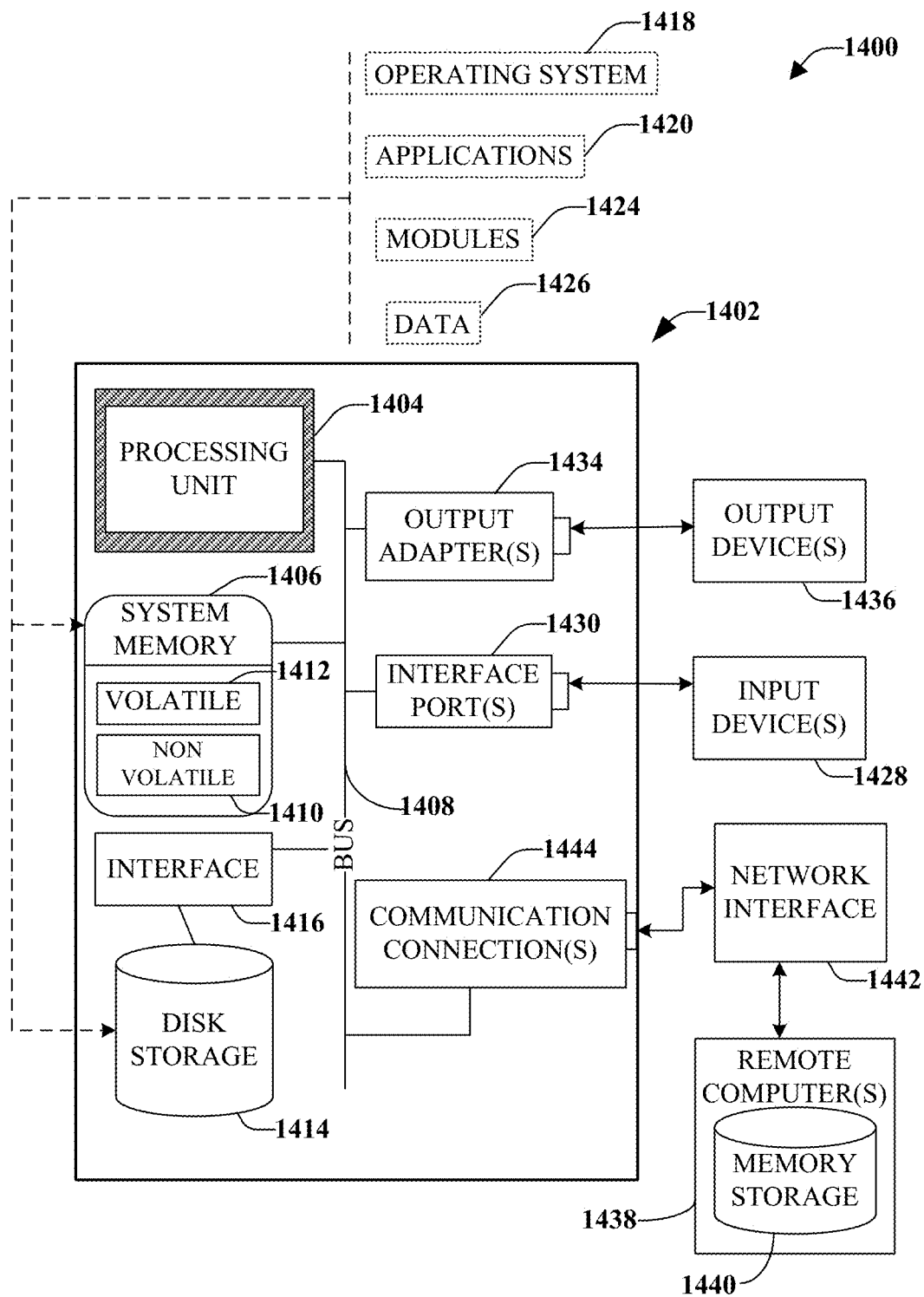
FIG. 14 illustrates a block diagram of a computer operable to execute the disclosed aspects.

Referring now to FIG. 14, illustrated is a block diagram of a computer operable to execute the disclosed aspects. In order to provide additional context for various aspects thereof, FIG. 14 and the following discussion are intended to provide a brief, general description of a suitable computing environment 1400 in which the various aspects of the embodiment(s) can be implemented. While the description above is in the general context of computer-executable instructions that may run on one or more computers, those skilled in the art will recognize that the various embodiments can be implemented in combination with other program modules and/or as a combination of hardware and software.

Generally, program modules include routines, programs, components, data structures, etc., that perform particular tasks or implement particular abstract data types. Moreover, those skilled in the art will appreciate that the disclosed aspects can be practiced with other computer system configurations, including single-processor or multiprocessor computer systems, single-board computers, minicomputers, mainframe computers, as well as personal computers, handheld computing devices, microprocessor-based or programmable consumer electronics, micro-controllers, embedded controllers, multi-core processors, and the like, each of which can be operatively coupled to one or more associated devices.

The illustrated aspects of the various embodiments may also be practiced in distributed computing environments where certain tasks are performed by remote processing devices that are linked through a communications network. In a distributed computing environment, program modules can be located in both local and remote memory storage devices. A computing platform can host or permit processing of all or many distinct logical agents. Alternatively, each agent may operate in a separate, networked processor that is centrally located or possibly located, or integrated with, the process or process equipment that it manages (e.g., a single-board computer running an oven agent may be embedded in an oven controller). Various degrees of centralized processing and distributed processing may be implemented.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, DRAM, flash memory, memory sticks or solid state memory, or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules, or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, microwave, RF, infrared and other wireless methods (e.g., IEEE 802.12x, IEEE 802.15.4, Bluetooth).

With reference again to FIG. 14, the illustrative environment 1400 for implementing various aspects includes a computer 1402, which includes a processing unit 1404, a system memory 1406 and a system bus 1408. The system bus 1408 couples system components including, but not limited to, the system memory 1406 to the processing unit 1404. The processing unit 1404 can be any of various commercially available processors. Dual microprocessors, custom processors, custom integrated-circuits, multi-core processor arrays, analog processors, pipeline processors, and other multi-processor architectures may also be employed as the processing unit 1404.

The system bus 1408 can be any of several types of bus structure that may further interconnect to a memory bus (with or without a memory controller), a peripheral bus, and a local bus using any of a variety of commercially available bus architectures. The system memory 1406 includes read-only memory (ROM) 1410 and random access memory (RAM) 1412. A basic input/output system (BIOS) is stored in a non-volatile memory 1410 such as ROM, EPROM, EEPROM, which BIOS contains the basic routines that help to transfer information between elements within the computer 1402, such as during start-up. The RAM 1412 can also include a high-speed RAM such as static RAM for caching data.

The computer 1402 further includes a disk storage 1414, which can include an internal hard disk drive (HDD) (e.g., EIDE, SATA), which internal hard disk drive may also be configured for external use in a suitable chassis (not shown), a magnetic floppy disk drive (FDD), (e.g., to read from or write to a removable diskette) and an optical disk drive (e.g., reading a CD-ROM disk or, to read from or write to other high capacity optical media such as the DVD). The hard disk drive, magnetic disk drive and optical disk drive can be connected to the system bus 1408 by a hard disk drive interface, a magnetic disk drive interface and an optical drive interface, respectively. The interface 1416 for external drive implementations includes at least one or both of Universal Serial Bus (USB) and IEEE 1094 interface technologies. Other external drive connection technologies are within contemplation of the various embodiments described herein.

The drives and their associated computer-readable media provide nonvolatile storage of data, data structures, computer-executable instructions, and so forth. For the computer 1402, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the illustrative operating environment, and further, that any such media may contain computer-executable instructions for performing the disclosed aspects.

A number of program modules can be stored in the drives and RAM, including an operating system 1418, one or more application programs 1420, other program modules 1424, and program data 1426. All or portions of the operating system, applications, modules, and/or data can also be cached in the RAM. It is to be appreciated that the various embodiments can be implemented with various commercially available operating systems or combinations of operating systems or may be implemented without an operating system.

A user can enter commands and information into the computer 1402 through one or more wired/wireless input devices 1428, such as a keyboard and a pointing device, such as a mouse. Other input devices (not shown) may include a microphone, an IR remote control, a joystick, a game pad, a stylus pen, touch screen, or the like. These and other input devices are often connected to the processing unit 1404 through an input device (interface) port 1430 that is coupled to the system bus 1408, but can be connected by other interfaces, such as a parallel port, an IEEE 1094 serial port, a game port, a USB port, an IR interface, etc. Additionally, the interface ports 1430 may include one or more channels of digital and/or analog input. The interface ports for analog signals will receive for example a voltage input coming from a process sensor such as a temperature sensor. The voltage input to the interface ports 1430 from the temperature sensor may vary linearly with the temperature of the sensor. The interface port will generate a digital value that corresponds to the voltage presented to the interface ports. The digital representation of the sensor value will be processed, averaged, or filtered as needed for use by applications 1420 and/or modules 1424. The interface ports may also receive digital inputs such from a switch or a button and similarly provide this digital value to applications 1420 and/or modules 1424.

A monitor or other type of display device is also connected to the system bus 1408 via an output (adapter) port 1434, such as a video adapter. In addition to the monitor, a computer typically includes other peripheral output devices 1436, such as speakers, printers, etc. The output adapters may also provide one or more digital and/or analog values for use by display, control, or other computer-based devices. For example, the output adapter 1434 could provide a voltage signal between about 0 volts and 10 volts that correspond to the desired speed of a mixing motor such that about 0 volts corresponds to around 0 rpm (revolutions per minute) and about 10 volts corresponds to around 1200 rpm.

The computer 1402 may operate in a networked environment using logical connections via wired and/or wireless communications to one or more remote computers, such as a remote computer(s) 1438. The remote computer(s) 1438 can be a workstation, a server computer, a router, a personal computer, portable computer, microprocessor-based entertainment appliance, a peer device or other common network node, and typically includes many or all of the elements described relative to the computer 1402, although, for purposes of brevity, only a memory/storage device 1440 is illustrated. Multiple computers may operate in an integrated manner to control a single (e.g., multi-step) production process. Process control tasks may be distributed across multiple computers. For example, an agent-based control architecture may have all the agents reside in a single computer-based controller or may have several or more agents reside in several computer-based controllers, or have each agent reside in a separate computer-based controller.

The remote computer(s) can have a network interface 1442 that enables logical connections to computer 1402. The logical connections include wired/wireless connectivity to a local area network (LAN) and/or larger networks, e.g., a wide area network (WAN). Such LAN and WAN networking environments are commonplace in offices and companies, and facilitate enterprise-wide computer networks, such as intranets, all of which may connect to a global communications network, e.g., the Internet.

When used in a LAN networking environment, the computer 1402 is connected to the local network through a wired and/or wireless communication network interface or adapter (communication connection(s)) 1444. The adaptor 1444 may facilitate wired or wireless communication to the LAN, which may also include a wireless access point disposed thereon for communicating with the wireless adaptor.

When used in a WAN networking environment, the computer 1402 can include a modem, or is connected to a communications server on the WAN, or has other means for establishing communications over the WAN, such as by way of the Internet. The modem, which can be internal or external and a wired or wireless device, is connected to the system bus 1408 via the serial port interface. In a networked environment, program modules depicted relative to the computer 1402, or portions thereof, can be stored in the remote memory/storage device 1440. It will be appreciated that the network connections shown are illustrative and other means of establishing a communications link between the computers can be used.

The computer 1402 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, and so forth), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11x (a, b, g, etc.) to provide secure, reliable, fast wireless connectivity. A Wi-Fi network can be used to connect computers to each other, to the Internet, and to wired networks (which use IEEE 802.3 or Ethernet).

Wi-Fi networks can operate in the unlicensed 2.4 and 5 GHz radio bands. IEEE 802.11 applies generally to wireless LANs and provides 1 or 2 Mbps transmission in the 2.4 GHz band using either frequency hopping spread spectrum (FHSS) or direct sequence spread spectrum (DSSS). IEEE 802.11a is an extension to IEEE 802.11 that applies to wireless LANs and provides up to 54 Mbps in the 5 GHz band. IEEE 802.11a uses an orthogonal frequency division multiplexing (OFDM) encoding scheme rather than FHSS or DSSS. IEEE 802.11b (also referred to as 802.11 High Rate DSSS or Wi-Fi) is an extension to 802.11 that applies to wireless LANs and provides 11 Mbps transmission (with a fallback to 5.5, 2 and 1 Mbps) in the 2.4 GHz band. IEEE 802.11g applies to wireless LANs and provides 20+ Mbps in the 2.4 GHz band. Products can contain more than one band (e.g., dual band), so the networks can provide real-world performance similar to the basic 10BaseT wired Ethernet networks used in many offices.

Figure 15:
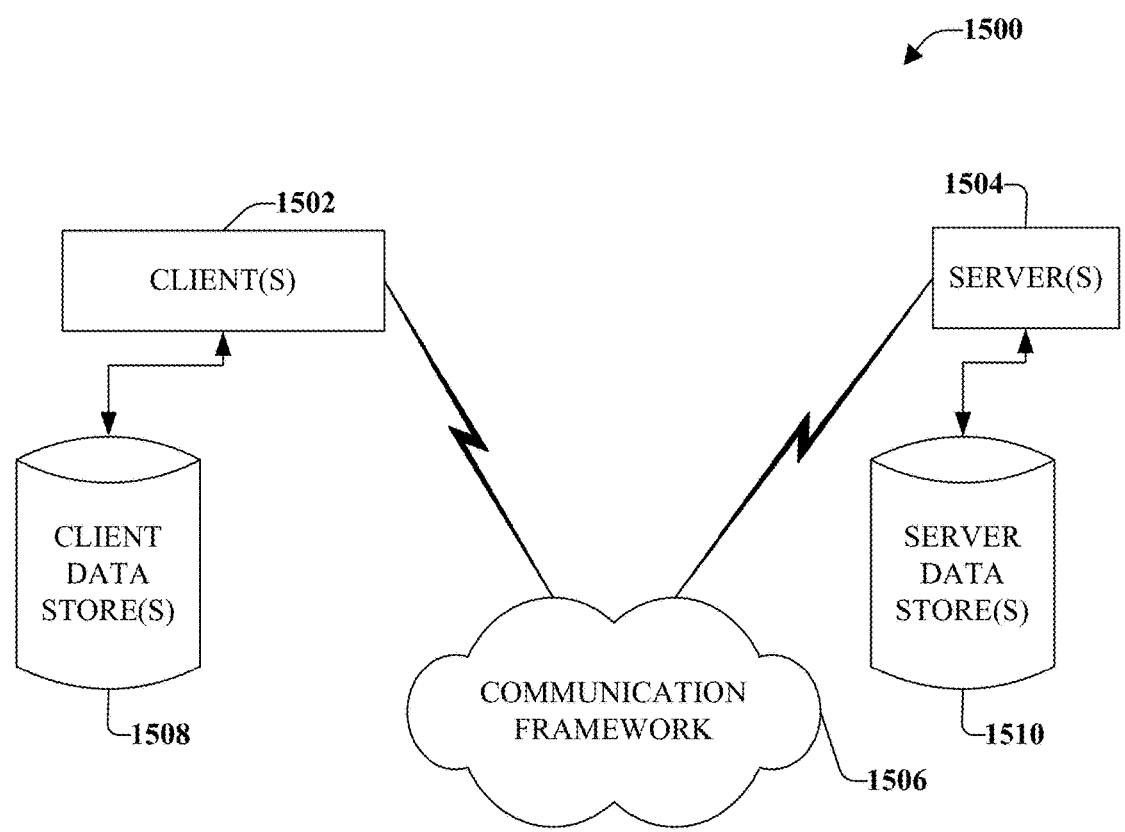
FIG. 15 illustrates a schematic block diagram of an exemplary computing environment, according to an aspect.

Referring now to FIG. 15, there is illustrated a schematic block diagram of an illustrative computing environment 1500 for processing the disclosed architecture in accordance with another aspect. The environment 1500 includes one or more client(s) 1502. The client(s) 1502 can be hardware and/or software (e.g., threads, processes, computing devices). The client(s) 1502 can house cookie(s) and/or associated contextual information in connection with the various embodiments, for example.

The environment 1500 also includes one or more server(s) 1504. The server(s) 1504 can also be hardware and/or software (e.g., threads, processes, computing devices). The servers 1504 can house threads to perform transformations in connection with the various embodiments, for example. One possible communication between a client 1502 and a server 1504 can be in the form of a data packet adapted to be transmitted between two or more computer processes. The data packet may include a cookie and/or associated contextual information, for example. The environment 1500 includes a communication framework 1506 (e.g., a global communication network such as the Internet) that can be employed to facilitate communications between the client(s) 1502 and the server(s) 1504.

Communications can be facilitated via a wired (including optical fiber) and/or wireless technology. The client(s) 1502 are operatively connected to one or more client data store(s) 1508 that can be employed to store information local to the client(s) 1502 (e.g., cookie(s) and/or associated contextual information). Similarly, the server(s) 1504 are operatively connected to one or more server data store(s) 1510 that can be employed to store information local to the servers 1504.

The various techniques described herein may be implemented in connection with hardware or software or, where appropriate, with a combination of both. As used in this application, the terms "component", "module", "object", "service", "model", "representation", "system", "interface", or the like are generally intended to refer to a computer-related entity, either hardware, a combination of hardware and software, software, or software in execution. For example, a component can be, but is not limited to being, a process running on a processor, a processor, a hard disk drive, a multiple storage drive (of optical and/or magnetic storage medium), an object, an executable, a thread of execution, a program, and/or a computer. By way of illustration, both an application running on a controller and the controller can be a component. One or more components can reside within a process and/or thread of execution and a component can be localized on one computer and/or distributed between two or more computers, industrial controllers, or modules communicating therewith. As another example, an interface can include I/O components as well as associated processor, application, and/or API components.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it can be noted that one or more components may be combined into a single component providing aggregate functionality or divided into several separate sub-components, and that any one or more middle layers, such as a management layer, may be provided to communicatively couple to such sub-components in order to provide integrated functionality. Any components described herein may also interact with one or more other components not specifically described herein but generally known by those of skill in the art.

In addition to the various embodiments described herein, it is to be understood that other similar embodiments can be used or modifications and additions can be made to the described embodiment(s) for performing the same or equivalent function of the corresponding embodiment(s) without deviating there from. Still further, multiple processing chips or multiple devices can share the performance of one or more functions described herein, and similarly, storage can be effected across a plurality of devices. Accordingly, the invention should not be limited to any single embodiment, but rather should be construed in breadth, spirit and scope in accordance with the appended claims.

The subject matter as described above includes various exemplary aspects. However, it should be appreciated that it is not possible to describe every conceivable component or methodology for purposes of describing these aspects. One of ordinary skill in the art may recognize that further combinations or permutations may be possible. Various methodologies or architectures may be employed to implement the subject invention, modifications, variations, or equivalents thereof. Accordingly, all such implementations of the aspects described herein are intended to embrace the scope and spirit of subject claims.

The word "exemplary" is used herein to mean serving as an example, instance, or illustration. For the avoidance of doubt, the subject matter disclosed herein is not limited by such examples. In addition, any aspect or design described herein as "exemplary" is not necessarily to be construed as preferred or advantageous over other aspects or designs, nor is it meant to preclude equivalent exemplary structures and techniques known to those of ordinary skill in the art.

To the extent that the term "includes" is used in either the detailed description or the claims, such term is intended to be inclusive in a manner similar to the term "comprising" as "comprising" is interpreted when employed as a transitional word in a claim. Furthermore, the term "or" as used in either the detailed description or the claims is intended to mean an inclusive "or" rather than an exclusive "or". That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

What is claimed is:

1. A system, comprising:
    a memory that stores computer executable components; and
    a processor that executes the computer executable components stored in the memory, the processor generates a process model and a biological model, the process model represents a simulation of a defined physical production process, and the biological model represents a simulation of biological activity of bacteria based on a determination that the bacteria is present within a first portion of the defined physical production process based on a measurement of the bacteria at the first portion;
    a controller that superimposes the biological model on the process model by integrating the biological model over the process model, wherein the controller models biochemical operations occurring at a second portion of the defined physical production process based on the biological model being superimposed on the process model and based on characteristics of the bacteria and an environment of the defined physical production process, wherein a growth of the bacteria in the biological model is simulated within the process model, and wherein a bacteria level at the second portion is unmeasured in the production process and is estimated based on the modeled bio-chemical operations; and an adjustment component that dynamically modifies at least a portion of a control sequence or a schedule of the second portion of the defined physical production process based, in part, upon the model of the bio-chemical operations at the second portion based on the bacteria level at the second portion being above a defined threshold level, wherein the modification by the adjustment component retains bacteria levels at the second portion below the defined threshold level.

2. The system of claim 1, wherein the controller creates a combined model based on the biological model being superimposed on the process model.

3. The system of claim 1, wherein the controller adjusts the operation of the defined physical production process by adjusting control parameters of the defined physical production process, process parameters of the defined physical production process, environmental parameters of the defined physical production process, equipment used in the defined physical production process, ingredients used in the defined physical production process, sequence of processing steps in the defined physical production process, a schedule of products made by the defined physical production process, or combinations thereof.

4. The system of claim 1, wherein the controller superimposes the biological model on the process model by operating the biological model and the process model in parallel.

5. The system of claim 1, wherein the process model comprises a representation of products of the defined production process, equipment used in the defined production process, time-based interactions between the products and the equipment, or combinations thereof.

6. The system of claim 1, wherein the biological model simulates bacteria levels within the defined physical production process.

7. The system of claim 1, further comprising a sensor that detects a type and a quantity of a biological species within the defined physical production process, wherein the controller adjusts the operation of the defined physical production process based at least in part upon the type of the biological species, the quantity of the biological species, or both.

8. The system of claim 1, wherein the controller adjusts the operation of the defined physical production process based at least in part on a quality parameter associated with the defined physical production process.

9. The system of claim 1, wherein the controller adjusts the operation of the defined physical production process based at least in part on an energy parameter associated with the defined physical production process.

10. A method, comprising:
superimposing, by a system comprising a processor, a biological model on a process model to create a combined model, wherein the superimposing comprises operating the biological model in parallel with the process model, and wherein the process model is a representation of a physical production process and the biological model is another representation of biological activity measured within the physical production process;

predicting, by the system, a bacteria level within the physical production process based on the combined model and on a bacteria growth determined based on the bacteria level and environmental conditions of the physical production process, wherein the predicting is based on knowledge of the biological activity measured within the physical production process, bacteria characteristics, and an environment of the physical production process; and generating, by the system, a command that adjusts a parameter of the physical production process, wherein the command is based at least in part on the predicted bacteria level and a desired bacteria level defined for the physical production process, and wherein the command retains a biological constraint, and satisfies a production parameter, of the physical production process.

11. The method of claim 10, further comprises adjusting, by the system, control parameters of the production process, process parameters of the physical production process, environmental parameters of the production process, equipment used in the physical production process, ingredients used in the physical production process, sequence of processing steps in the physical production process, a schedule of products made by the production process, or any combinations thereof based on the command.

12. The method of claim 10, wherein the generating the command comprises:
generating a plurality of potential operating scenarios that satisfy an objective function of the physical production process and a constraint of the physical production process; and
selecting one of the plurality of potential operating scenarios, wherein the command implements the selected operating scenario.

13. The method of claim 10, wherein the command is based at least in part on a quality parameter associated with the physical production process.

14. The method of claim 10, wherein the command is based at least in part on an energy parameter defined for the physical production process.

15. The method of claim 10, wherein the superimposing the biological model on the process model comprises operating the biological model and the process model substantially simultaneously, and wherein the biological model is defined with respect to the process model.

16. A method, comprising:
superimposing, by a system comprising a processor, a biological model on a process model, wherein the superimposing comprises executing the biological model in parallel with the process model, and wherein the process model is a simulation of a physical production process and the biological model is a simulation of biological activity in the process model based on measuring biological activity within the physical production process;
modeling, by the system, bio-chemical operations occurring in the physical production process based on the biological model being superimposed on the process model;
predicting, by the system, a first bacteria level determined to be occurring within the physical production process based at least in part on the biological model being superimposed on the process model, wherein the predicting the first bacteria level is based on an initial bacteria level and a change to the initial bacteria level due to a defined cooking regimen of the physical production process; and adjusting, by the system, a process parameter of the physical production process based on a comparison between the first bacteria level and a defined threshold bacteria level, wherein the process parameter is a cooking temperature that is increased based on the first bacteria level being above the defined threshold bacteria level or that is maintained based on the first bacteria level being below the defined threshold bacteria level.

17. The method of claim 16, further comprising:

measuring, by the system, a second bacteria level within the physical production process with a sensor located within the physical production process; and adjusting, by the system, the biological model, the process model, or both, in a feedback loop based at least in part on another comparison between the first bacteria level and the second bacteria level, wherein the adjusting the biological model, the process model, or both, comprises adapting the biological model, the process model, or both, to reflect changes in bacteria species, metabolic rates, environmental conditions, or any combination thereof, affecting the physical production process.

18. The method of claim 17, further comprises introducing, by the system, a known stimulus into the physical production process, wherein predicting the first bacteria level comprises predicting the first bacteria level in response to the known stimulus, and measuring the second bacteria level comprises measuring the second bacteria level within the physical production process in response to the known stimulus.

19. The method of claim 16, wherein the superimposing the biological model on the process model comprises creating a combined model that comprises the biological model defined with respect to the process model.

20. The method of claim 17, wherein the predicting the first bacteria level comprises simulating the first bacteria level at multiple stages within the process model, and measuring the second bacteria level comprises measuring the second bacteria level occurring at the multiple stages in the physical production process.

* * * * *